(12) United States Patent
Nguyen et al.

(10) Patent No.: US 8,974,446 B2
(45) Date of Patent: Mar. 10, 2015

(54) ULTRASOUND ABLATION APPARATUS WITH DISCRETE STAGGERED ABLATION ZONES

(75) Inventors: Tho Hoang Nguyen, Huntington Beach, CA (US); Cary Hata, Irvine, CA (US); Alan De La Rama, Cerritos, CA (US); Vivian Tran, Laguna Niguel, CA (US); Peter C. Chen, Irvine, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 1060 days.

(21) Appl. No.: 13/019,563

(22) Filed: Feb. 2, 2011

(65) Prior Publication Data

US 2011/0137298 A1 Jun. 9, 2011

Related U.S. Application Data

(63) Continuation-in-part of application No. 11/975,822, filed on Oct. 22, 2007, now abandoned, and a continuation-in-part of application No. 11/583,263, filed on Oct. 19, 2006, now abandoned, said (Continued)

(51) Int. Cl.
*A61B 18/04* (2006.01)
*A61B 17/22* (2006.01)
(Continued)

(52) U.S. Cl.
CPC ............... *A61B 17/2202* (2013.01); *A61B 5/01* (2013.01); *A61B 5/0402* (2013.01); *A61B 5/6852* (2013.01);

(Continued)

(58) Field of Classification Search
USPC .................. 606/27; 607/96, 101, 154–156; 600/459; 601/2, 3
See application file for complete search history.

(56) References Cited

U.S. PATENT DOCUMENTS

| 3,650,277 A | 3/1972 | Sjostrand et al. |
| 4,658,819 A | 4/1987 | Harris et al. |

(Continued)

FOREIGN PATENT DOCUMENTS

| EP | 0 911 059 A2 | 4/1999 |
| EP | 1 042 990 A1 | 10/2000 |

(Continued)

OTHER PUBLICATIONS

Pappone et al., Circumferential Radiofrequency Ablation of Pulmonary Vein Ostia, Circulation (2000) 102:2619-2628.

(Continued)

*Primary Examiner* — Joseph Stoklosa
*Assistant Examiner* — Jocelyn D Ram
(74) *Attorney, Agent, or Firm* — Armstrong Teasdale LLP

(57) ABSTRACT

An ablation apparatus comprises an ultrasonic transducer which includes a piezoelectric element having a cylindrical shape; a plurality of external electrodes disposed on the outer surface of the piezoelectric element; and at least one internal electrode disposed on the inner surface of the piezoelectric element. The at least one internal electrode provides corresponding internal electrode portions that are disposed opposite the external electrodes with respect to the piezoelectric element, the external electrodes and the at least one internal electrode to be energized to apply an electric field across the piezoelectric element. The ultrasonic ablation zones of the external electrodes are distributed in a staggered configuration so as to span one or more open arc segments around the longitudinal axis, and the ultrasound ablation zones of all external electrodes projected longitudinally onto any lateral plane which is perpendicular to the longitudinal axis span a substantially closed loop around the longitudinal axis.

20 Claims, 19 Drawing Sheets

Related U.S. Application Data application No. 11/975,822 is a continuation of application No. 10/845,798, filed on May 15, 2004, now Pat. No. 7,285,116, said application No. 11/583,263 is a continuation of application No. 09/975,269, filed on Oct. 11, 2001, now Pat. No. 6,671,533.

(51) Int. Cl.

| | | |
|---|---|---|
| *A61N 7/02* | (2006.01) | |
| *A61B 5/01* | (2006.01) | |
| *A61B 5/0402* | (2006.01) | |
| *A61B 5/00* | (2006.01) | |
| *A61B 17/00* | (2006.01) | |
| *A61B 17/32* | (2006.01) | |
| *A61B 18/00* | (2006.01) | |
| *A61N 7/00* | (2006.01) | |

(52) U.S. Cl.
CPC .............. *A61B 2017/00243* (2013.01); *A61B 2017/00247* (2013.01); *A61B 2017/22021* (2013.01); *A61B 2017/320084* (2013.01); *A61B 2018/00392* (2013.01); *A61N 7/022* (2013.01); *A61N 2007/003* (2013.01); *A61N 2007/0078* (2013.01)
USPC ................................. 606/27; 600/459; 601/2

(56) References Cited

U.S. PATENT DOCUMENTS

| | | | |
|---|---|---|---|
| 5,035,694 A | 7/1991 | Kasprzyk et al. | |
| 5,255,679 A | 10/1993 | Imran | |
| 5,295,484 A | 3/1994 | Marcus et al. | |
| 5,300,068 A | 4/1994 | Rosar et al. | |
| 5,368,591 A | 11/1994 | Lennox et al. | |
| 5,387,233 A | 2/1995 | Alferness et al. | |
| 5,465,717 A | 11/1995 | Imran et al. | |
| 5,531,779 A | 7/1996 | Dahl et al. | |
| 5,545,161 A | 8/1996 | Imran | |
| 5,582,609 A | 12/1996 | Swanson et al. | |
| 5,598,848 A | 2/1997 | Swanson et al. | |
| 5,607,462 A | 3/1997 | Imran | |
| 5,620,479 A | 4/1997 | Diederich | |
| 5,628,313 A | 5/1997 | Webster, Jr. | |
| 5,676,662 A | 10/1997 | Fleischhacker et al. | |
| 5,676,693 A | 10/1997 | LaFontaine | |
| 5,697,927 A | 12/1997 | Imran et al. | |
| 5,707,400 A | 1/1998 | Terry, Jr. et al. | |
| 5,735,811 A | 4/1998 | Brisken | |
| 5,738,683 A | 4/1998 | Osypka | |
| 5,769,077 A | 6/1998 | Lindegren | |
| 5,772,590 A | 6/1998 | Webster, Jr. | |
| 5,782,828 A | 7/1998 | Chen et al. | |
| 5,836,947 A | 11/1998 | Fleischman et al. | |
| 5,846,218 A | 12/1998 | Brisken et al. | |
| 5,860,920 A | 1/1999 | McGee et al. | |
| 5,885,278 A | 3/1999 | Fleischman | |
| 5,891,136 A | 4/1999 | McGee et al. | |
| 5,893,885 A | 4/1999 | Webster, Jr. | |
| 5,897,553 A | 4/1999 | Mulier et al. | |
| 5,897,554 A | 4/1999 | Chia et al. | |
| 5,921,982 A | 7/1999 | Lesh et al. | |
| 5,951,471 A | 9/1999 | De La Rama et al. | |
| 5,954,649 A | 9/1999 | Chia et al. | |
| 5,954,719 A | 9/1999 | Chen et al. | |
| 5,971,980 A | 10/1999 | Sherman | |
| 5,971,983 A | 10/1999 | Lesh | |
| 5,997,532 A | 12/1999 | McLaughlin et al. | |
| 6,004,269 A | 12/1999 | Crowley et al. | |
| 6,007,530 A | 12/1999 | Dornhofer et al. | |
| 6,012,457 A | 1/2000 | Lesh | |
| 6,016,437 A | 1/2000 | Tu et al. | |
| 6,024,740 A | 2/2000 | Lesh et al. | |
| 6,071,274 A | 6/2000 | Thompson et al. | |
| 6,071,279 A | 6/2000 | Whayne et al. | |
| 6,071,282 A | 6/2000 | Fleischman | |
| 6,073,048 A | 6/2000 | Kieval et al. | |
| 6,083,170 A | 7/2000 | Ben-Haim | |
| 6,096,037 A | 8/2000 | Mulier et al. | |
| 6,117,101 A | 9/2000 | Diederich et al. | |
| 6,120,476 A | 9/2000 | Fung et al. | |
| 6,120,500 A | 9/2000 | Bednarek et al. | |
| 6,161,543 A | 12/2000 | Cox et al. | |
| 6,164,283 A | 12/2000 | Lesh | |
| 6,178,349 B1 | 1/2001 | Kieval | |
| 6,200,312 B1 | 3/2001 | Zikorus et al. | |
| 6,206,831 B1 | 3/2001 | Suorsa et al. | |
| 6,206,842 B1 | 3/2001 | Tu et al. | |
| 6,214,002 B1 | 4/2001 | Fleischman et al. | |
| 6,216,044 B1 | 4/2001 | Kordis | |
| 6,233,491 B1 | 5/2001 | Kordis et al. | |
| 6,241,666 B1 | 6/2001 | Pomeranz et al. | |
| 6,241,727 B1 | 6/2001 | Tu et al. | |
| 6,245,064 B1 | 6/2001 | Lesh et al. | |
| 6,264,654 B1 | 7/2001 | Swartz et al. | |
| 6,283,951 B1 | 9/2001 | Flaherty et al. | |
| 6,287,608 B1 | 9/2001 | Levin et al. | |
| 6,292,695 B1 | 9/2001 | Webster, Jr. et al. | |
| 6,315,777 B1 | 11/2001 | Comben | |
| 6,315,778 B1 | 11/2001 | Gambale et al. | |
| 6,322,559 B1 | 11/2001 | Daulton et al. | |
| 6,325,797 B1 | 12/2001 | Stewart et al. | |
| 6,460,545 B2 | 10/2002 | Kordis | |
| 6,522,926 B1 | 2/2003 | Kieval et al. | |
| 6,524,251 B2 | 2/2003 | Rabiner et al. | |
| 6,529,756 B1 | 3/2003 | Phan et al. | |
| 6,579,288 B1 | 6/2003 | Swanson et al. | |
| 6,602,242 B1 | 8/2003 | Fung et al. | |
| 6,613,045 B1 | 9/2003 | Laufer et al. | |
| 6,616,624 B1 | 9/2003 | Kieval | |
| 6,635,054 B2 | 10/2003 | Fjield et al. | |
| 6,652,517 B1 | 11/2003 | Hall et al. | |
| 6,656,174 B1 | 12/2003 | Hedge et al. | |
| 6,669,655 B1 * | 12/2003 | Acker et al. ................. | 601/2 |
| 6,671,533 B2 | 12/2003 | Chen et al. | |
| 6,672,312 B2 | 1/2004 | Acker | |
| 6,699,231 B1 | 3/2004 | Sterman et al. | |
| 6,748,255 B2 | 6/2004 | Fuimaono et al. | |
| 6,793,635 B2 * | 9/2004 | Ryan et al. ................. | 601/2 |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,653,438 B2 | 1/2010 | Deem et al. | |
| 7,674,256 B2 | 3/2010 | Marrouche et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 * | 1/2013 | Demarais et al. ................. | 128/898 |
| 8,442,639 B2 | 5/2013 | Walker et al. | |
| 8,454,594 B2 | 6/2013 | Demarais et al. | |
| 8,545,495 B2 | 10/2013 | Scheib | |
| 2002/0022833 A1 | 2/2002 | Maguire et al. | |
| 2002/0026187 A1 | 2/2002 | Swanson | |
| 2002/0068885 A1 | 6/2002 | Harhen et al. | |
| 2002/0115990 A1 | 8/2002 | Acker | |
| 2002/0120304 A1 | 8/2002 | Mest | |
| 2002/0177765 A1 | 11/2002 | Bowe et al. | |

(56) References Cited

U.S. PATENT DOCUMENTS

| | | | |
|---|---|---|---|
| 2003/0013968 A1* | 1/2003 | Fjield et al. | 600/459 |
| 2003/0050681 A1 | 3/2003 | Pianca et al. | |
| 2003/0060858 A1 | 3/2003 | Kieval et al. | |
| 2003/0073891 A1* | 4/2003 | Chen et al. | 600/374 |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0049148 A1 | 3/2004 | Rodriguez et al. | |
| 2004/0215186 A1 | 10/2004 | Cornelius et al. | |
| 2005/0010095 A1 | 1/2005 | Stewart et al. | |
| 2005/0096647 A1* | 5/2005 | Steinke et al. | 606/41 |
| 2005/0165388 A1 | 7/2005 | Bhola | |
| 2005/0197577 A1 | 9/2005 | Makin et al. | |
| 2005/0256518 A1 | 11/2005 | Rama et al. | |
| 2005/0288730 A1 | 12/2005 | Deem et al. | |
| 2006/0064081 A1 | 3/2006 | Rosinko | |
| 2006/0089678 A1 | 4/2006 | Shalev | |
| 2006/0184072 A1* | 8/2006 | Manna | 601/2 |
| 2007/0135875 A1 | 6/2007 | Demarais et al. | |
| 2008/0177205 A1* | 7/2008 | Rama et al. | 601/3 |
| 2008/0255478 A1 | 10/2008 | Burdette | |
| 2009/0076409 A1 | 3/2009 | Wu et al. | |
| 2010/0016762 A1 | 1/2010 | Thapliyal et al. | |
| 2010/0094209 A1 | 4/2010 | Drasler et al. | |
| 2010/0168737 A1 | 7/2010 | Grunewald | |
| 2010/0191112 A1* | 7/2010 | Demarais et al. | 600/439 |
| 2010/0222854 A1* | 9/2010 | Demarais et al. | 607/99 |
| 2010/0249773 A1 | 9/2010 | Clark et al. | |
| 2010/0268307 A1 | 10/2010 | Demarais et al. | |
| 2010/0286684 A1 | 11/2010 | Hata et al. | |
| 2011/0004087 A1 | 1/2011 | Fish et al. | |
| 2011/0034808 A1* | 2/2011 | Chen et al. | 600/459 |
| 2011/0118726 A1* | 5/2011 | De La Rama et al. | 606/33 |
| 2011/0137298 A1 | 6/2011 | Nguyen et al. | |
| 2011/0160720 A1 | 6/2011 | Johnson | |
| 2011/0213231 A1 | 9/2011 | Hall et al. | |
| 2011/0251527 A1* | 10/2011 | Kushculey et al. | 601/2 |
| 2011/0257562 A1* | 10/2011 | Schaer | 601/2 |
| 2011/0257641 A1 | 10/2011 | Hastings et al. | |
| 2011/0264011 A1 | 10/2011 | Wu et al. | |
| 2011/0264086 A1 | 10/2011 | Ingle | |
| 2012/0143097 A1 | 6/2012 | Pike, Jr. | |
| 2012/0143298 A1 | 6/2012 | Just et al. | |
| 2012/0296232 A1 | 11/2012 | Ng | |
| 2012/0323233 A1 | 12/2012 | Maguire et al. | |
| 2013/0116737 A1 | 5/2013 | Edwards et al. | |
| 2013/0131743 A1 | 5/2013 | Yamasaki et al. | |
| 2013/0144251 A1 | 6/2013 | Sobotka | |
| 2013/0172715 A1 | 7/2013 | Just et al. | |
| 2014/0163540 A1* | 6/2014 | Iyer et al. | 606/27 |
| 2014/0207136 A1* | 7/2014 | De La Rama et al. | 606/41 |

FOREIGN PATENT DOCUMENTS

| | | |
|---|---|---|
| WO | 95/13111 A1 | 5/1995 |
| WO | 9719645 A1 | 6/1997 |
| WO | 97/45157 | 12/1997 |
| WO | 00/56237 A2 | 9/2000 |
| WO | 00/66020 | 11/2000 |
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Lin et al., Pulmonary Vein Morphology in Patients with Paroxysmal Atrial Fibrillation Initiated by Ectopic Beats Originating from the Pulmonary Veins, Circulation, (2000) 101:1274-1281.

Natale et al., First Human Experience with Pulmonary Vein Isolation Using a Through-the-Balloon Circumferential Ultrasound Ablation System for Recurrent Atrial Fibrillation, Circulation, (2000) 102:1879-1882.

Zazgornik, Jan et al, Bilateral Nephrectomy: The Best, but Often Overlooked, Treatment for Refractory Hypertension in Hemodialysis Patients, AJH 1998; 11:1364-1370.

Abboud, Francois M., The Sympathetic System in Hypertension, State-of-the-Art Review, Hypertension Journal of the American Heart Association, Hypertension 4 (suppl II): II-208-II-225, 1982.

Allen, Edgar V., Sympathectomy for Essential Hypertension, Circulation Journal of the American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

Ardian, Inc., Ardian(R) Receives 2010 EuroPCR Innovation Award and Demonstrates Further Durability of Renal Denervation Treatment for Hypertension, PR Newswire, Jun. 3, 2010.

Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.

Badoer, Emilio et al, Cardiac Afferents Play the Dominant Role in Renal Nerve Inhibition Elicited by Volume Expansion in the Rabbit, American Journal of Physiology, 1998, R383-R388.

Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.

Bao, Gang et al, Blood Pressure Response to Chronic Episodic Hypoxia: Role of the Sympathetic Nervous System, American Journal of Physiology, 1997, 95-101.

Barajas, Luciano et al, Anatomy of the Renal Innervation: Intrarenal Aspects and Ganglia of Origin, Canadian Journal of Physiology and Pharmacology, vol. 70, No. 5, May 1992, 735-749.

Barajas, Luciano et al, Monoaminergic Innervation of the Rat Kidney: A Quantitative Study, American Journal of Physiology, vol. 259, No. 3, Sep. 1990, F503-F511.

Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.

Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.

Bello-Reuss, Elsa et al, Effects of Acute Unilateral Renal Denervation in the Rat, The Journal of Clinical Investigation, vol. 56, Jul. 1975, 208-217.

Benito, Fernando et al, Radiofrequency Catheter Ablation of Accessory Pathways in Infants, Heart, 1997, 78, 160-162.

Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.

Bertog, Stefan C. et al, Renal Denervation for Hypertension, JACC: Cardiovascular Interventions, vol. 5, No. 3, Mar. 2012, 249-258.

Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.

Blankestijn, Peter J. et al, Renal Denervation: Potential Impact on Hypertension in Kidney Disease?, Nephrol Dial Transplant (2011) 0: 1-3.

Blankestijn, Peter J. et al, Sympathetic Overactivity in Renal Failure Controlled by ACE Inhibition: Clinical Significance, Nephrol Dial Transplant, 2000, 15, 755-758.

Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.

(56) References Cited

OTHER PUBLICATIONS

Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9:741-742.
Campese, Vito M. et al, Neurogenic Factors in Renal Hypertension, Current Hypertension Reports, 2002 4:256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1)14-8.
Chabanier, H. et al, On the Decapsulation and Neurectomy of the Kidnsey in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation a Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.

(56) References Cited

OTHER PUBLICATIONS

Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.

Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.-Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catherization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.

(56) References Cited

OTHER PUBLICATIONS

Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 ,pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14 (4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, Jan. 10-15, 2002.
Pearce, John A. et al, Blood Vessel Architectural Features and Their Effect on Thermal Phenomena, Critical Reviews, vol. CR75, 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis a Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).

(56) References Cited

OTHER PUBLICATIONS

Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After Symplicity HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 (May/Jun. 1999): pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of The American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of The American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65,729-734.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.

(56) References Cited

OTHER PUBLICATIONS

Dubuc, Marc et al, Feasibility of Cardiac Cryoablation Using a Transvenous Steerable Electrode Catheter, Journal of Interventional Cardiac Electrophysiology, 1998, 2: 285-292.

Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.

Esler, M. et al, Sympathetic Nerve Activity and Neurotransmitter Release in Humans: Translation from Pathophysiology into Clinical Practice, Scandinavian Physiological Society, 2003, 177, 275-284.

Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.

Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.

Evelyn, Kenneth A. et al, Effect of Thoracolumbar Sympathectomy on the Clinical Course of Primary (Essential) Hypertension, American Journal of Medicine, Feb. 1960, 188-221.

Freyberg, R. H. et al, The Effect on the Kidney of Bilateral Splanchnicectomy in Patients with Hypertension, The Journal of Clinical Investigation, vol. 16, Issue 1, Jan. 1937, 49-65.

Gafoor, Sameer et al, Nonresponders to Renal Denervation for Resistant Hypertension, Endovascular Today, Oct. 2013, 63-70.

Garel, L. et al, Fatal Outcome After Ethanol Renal Ablation in Child with End-Stage Kidneys; AJR 146:593-594, Mar. 1986.

Gazdar, A. F. et al, Neural Degeneration and Regeneration in Human Renal Transplants, The New England Journal of Medicine, vol. 238, No. 5, Jul. 1970, 222-224.

Goldberg, Michael R. et al, Reconstructive Vascular Surgery for Renovascular Hypertension, Can Med Assoc J. Feb. 2, 1974;110(3):275-80.

Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.

Gorisch, Wolfram et al, Heat-Induced Contraction of Blood Vessels, Lasers in Surgery and Medicine 2:I-13 (1982).

Grassi, Guido et al, Baroreflex Control of Sympathetic Nerve Activity in Essential and Secondary Hypertension, Hypertension Journal of The American Heart Association, 1998;31:68-72.

Grassi, Guido et al, Dissociation Between Muscle and Skin Sympathetic Nerve Activity in Essential Hypertension, Obesity, and Congestive Heart Failure, Hypertension. 1998;31:64-67.

Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.

Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.

Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.

Guyton, Arthur C., Blood Pressure Control Special Role of the Kidneys and Body Fluids, Science, vol. 252, Jun. 1991, 1813-1816.

Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.

Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.

Hall, J.E. et al, Role of Sympathetic Nervous System and Neuropeptides in Obesity Hypertension, Brazilian Journal of Medical and Biological Research, 2000, 33:605-618.

Hall, John E., The Kidney, Hypertension, and Obesity, Hypertension. 2003;41:625-633.

Hall, Winthrop H. et al, Combined Embolization and Percutaneous Radiofrequency Ablation of a Solid Renal Tumor, American Journal of Roentgenology, 174, Jun. 2000, 1592-1594.

Hamm, Christian et al, Confluence, Issue eight, Apr. 2014.

Han, Young-Min et al, Renal Artery Embolization with Diluted Hot Contrast Medium: An Experimental Study, Journal of Vascular and Interventional Radiology, Jul. 2001;12(7):862-868.

Hansen, Jesper Melchoir et al, The Transplanted Human Kidney Does Not Achieve Functional Reinnervation, Clinical Science, (1994) 87, 13-20.

Heuer, George J., The Surgical Treatment of Essential Hypertension, Annals of Surgery, Oct. 1936, vol. 104, No. 3, 771-786.

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of The American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.

Howard, James P. et al, Size of Blood Pressure Reduction from Renal Denervation: Insights from Meta-Analysis of Antihypertensive Drug Trials of 4121 Patients with Focus on Trial Design: the Converge Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, Shoei K. Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of The American Heart Association, 1998;32:249-254.

Humpreys, Michael H., Renal Nerves and CKD: Is Renal Denervation the Answer?, Journal of The American Socity of Nephrology, 2012, 23: 1-3.

International Search Report and Written Opinion for Application No. PCT/US2010/054637.

International Search Report and Written Opinion for Application No. PCT/US2010/054684.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

* cited by examiner

SECTION A-A

SECTION B-B

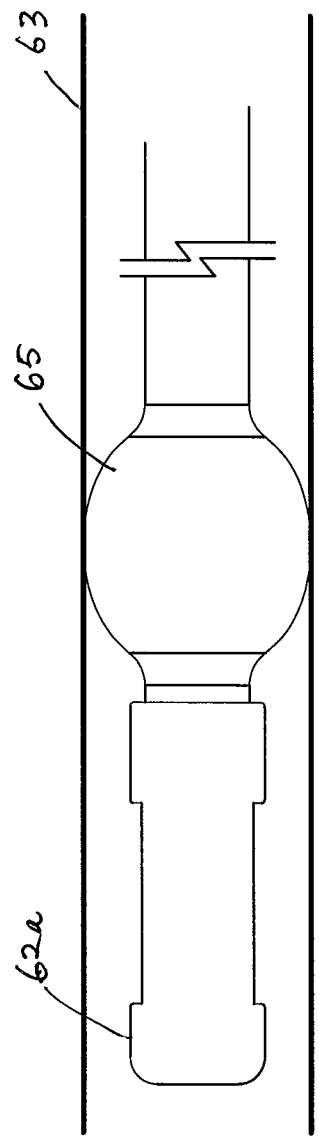

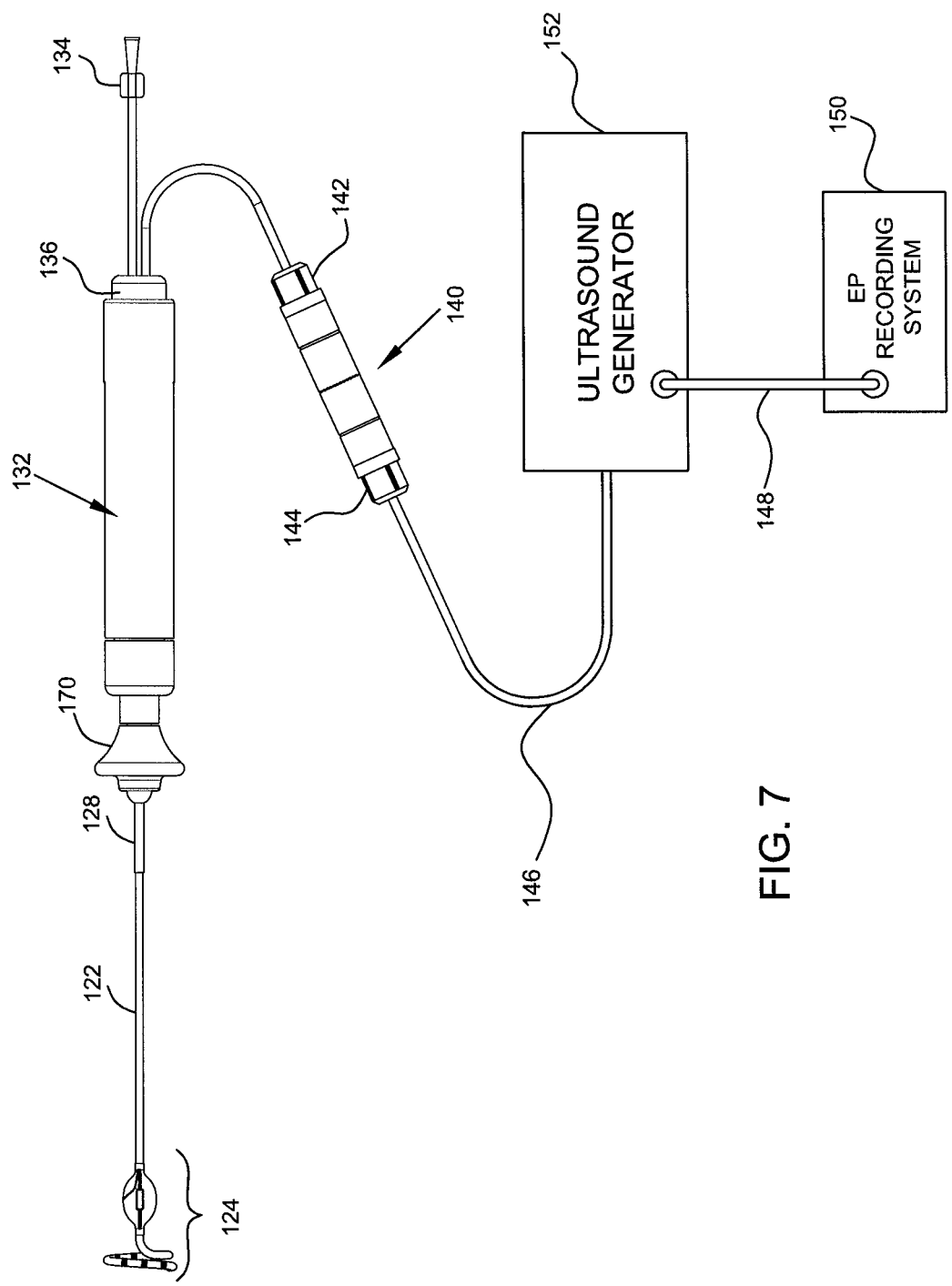

SECTION A-A

SECTION B-B

ULTRASOUND ABLATION APPARATUS WITH DISCRETE STAGGERED ABLATION ZONES

RELATED APPLICATIONS

This application is a continuation-in-part of U.S. patent application Ser. No. 11/975,822, filed on Oct. 22, 2007, which is a continuation of U.S. patent application Ser. No. 10/845,798, filed on May 15, 2004 (now U.S. Pat. No. 7,285,116). This application is also a continuation-in-part of U.S. patent application Ser. No. 11/583,263, filed on Oct. 19, 2006, which is a continuation of U.S. patent application Ser. No. 09/975,269, filed on Oct. 11, 2001 (now U.S. Pat. No. 6,671,533). The entire disclosures of the above are incorporated herein by reference.

BACKGROUND OF THE INVENTION

The present invention relates generally to ablation devices and, more specifically, to an assembly of ablation elements arranged in a staggered configuration.

Hypertension is a major global public health concern. An estimated 30-40% of the adult population in the developed world suffers from this condition. Furthermore, its prevalence is expected to increase, especially in developing countries. Diagnosis and treatment of hypertension remain suboptimal, even in developed countries. Despite the availability of numerous safe and effective pharmacological therapies, including fixed-drug combinations, the percentage of patients achieving adequate blood-pressure control to guideline target values remains low. Much failure of the pharmacological strategy to attain adequate blood-pressure control is attributed to both physician inertia and patient non-compliance and non-adherence to a lifelong pharmacological therapy for a mainly asymptomatic disease. Thus, the development of new approaches for the management of hypertension is a priority. These considerations are especially relevant to patients with so-called resistant hypertension (i.e., those unable to achieve target blood-pressure values despite multiple drug therapies at the highest tolerated dose). Such patients are at high risk of major cardiovascular events.

Renal sympathetic efferent and afferent nerves, which lie within and immediately adjacent to the wall of the renal artery, are crucial for initiation and maintenance of systemic hypertension. Indeed, sympathetic nerve modulation as a therapeutic strategy in hypertension had been considered long before the advent of modern pharmacological therapies. Radical surgical methods for thoracic, abdominal, or pelvic sympathetic denervation had been successful in lowering blood pressure in patients with so-called malignant hypertension. However, these methods were associated with high perioperative morbidity and mortality and long-term complications, including bowel, bladder, and erectile dysfunction, in addition to severe postural hypotension. Renal denervation is the application of a chemical agent, or a surgical procedure, or the application of energy to partially or completely damage renal nerves to partially or completely block the renal nerve activities. Renal denervation reduces or completely block renal sympathetic nerve activity, increases renal blood flow (RBF), and decreases renal plasma norepinephrine (NE) content.

That renal denervation can prevent or delay hypertension was known as early as 1936. See Heuer G J. The surgical treatment of essential hypertension, *Annals of Surgery*, 1936; 104 (4): 771-786. The surgical denervation, i.e., sympathectomy, was applied for treatment of hypertension, though with many clinical complications. Catheter renal intervention was developed much earlier, and catheter for renal angiography was introduced in 1950. Numerous publications are available on the application of electrical energy to renal nerves and the renal responses. The earliest insight into the influence of the renal nerves on renal function is that of Claude Bernard in 1859. RF ablation has been used for tumor removal for many years and there have been a great amount of publications on pulmonary venous (PV) ablation for treating AF since 1998. Intra-blood vessel RF ablation may damage nerves as documented in patent publications in 2002. See, e.g., Acker D., WO/2002/085192, Improvement in Ablation Therapy, CIPI, Oct. 31, 2002; see also Smithwick R H, Surgical treatment of hypertension, *Am J Med* 1948, 4:744-759; Allen E V, Sympathectomy for essential hypertension, *Circulation,* 1952, 6:131-140; Smithwick R H, Thompson J E, Splanchnicectomy for essential hypertension: results in 1,266 cases, *JAMA,* 1953, 152:1501-1504; Morrissey D M, Brookes V S, Cooke W T, Sympathectomy in the treatment of hypertension, review of 122 cases, *Lancet,* 1953, 1:403-408; Whitelaw G P, Kinsey D, Smithwick R H, Factors influencing the choice of treatment in essential hypertension: surgical, medical, or a combination of both, *Am J Surg,* 1964, 107:220-231; Gottschalk C W, Renal nerves and sodium excretion, Ann. Rev. Physiol., 1979, 41:229-40; Mancia G., Grassi G., Giannattasio C., Seravalle G., Sympathetic activation in the pathogenesis of hypertension and progression of organ damage, *Hypertension* 1999, 34 (4 Pt 2): 724-728; DiBona G F, Sympathetic nervous system and the kidney in hypertension, *Curr Opin Nephrol Hypertens,* 2002, 11(2):197-200; Haïssaguerre M et al., "Spontaneous initiation of atrial fibrillation by ectopic beats originating in the pulmonary veins," *New England Journal of Medicine,* 1998, 339:659-666; Chen, S A et al., "Initiation of atrial fibrillation by ectopic beats originating from the pulmonary veins: electrophysiological characteristics, pharmacological responses, and effects of radiofrequency ablation," *Circulation,* 1999, 100:1879-1886; and Shah D C, Haïssaguerre M, Jais P, Catheter ablation of pulmonary vein foci for atrial fibrillation: pulmonary vein foci ablation for atrial fibrillation, *Thorac Cardiovasc Surg,* 1999, 47(suppl. 3):352-356. The entire disclosures of these publications are incorporate herein by reference.

The object of renal denervation is to neutralize the effect of renal sympathetic system which is involved in arterial hypertension. Device-based renal denervation may achieve such objective, but may produce possible complications of renal artery/vein stenosis. Thus, there is a need for a device that can perform renal denervation with reduced risk of renal artery/vein stenosis.

BRIEF SUMMARY OF THE INVENTION

Embodiments of the present invention are directed to an assembly of staggered ablation elements which are energized to produce ablation zones that span one or more open arc segments around the longitudinal axis, but the ablation zones of all the ablation elements projected longitudinally onto any lateral plane which is perpendicular to the longitudinal axis span a substantially closed loop around the longitudinal axis. The renal nerves are oriented generally longitudinally. Because the ablation zones do not form a closed loop, the risk of renal artery/vein stenosis is reduced or eliminated. On the other hand, because the ablation zones of all the ablation elements projected longitudinally onto any lateral plane span a substantially closed loop, a substantially complete renal denervation is achieved.

In accordance with an aspect of the present invention, an ablation apparatus comprises an ultrasonic transducer which includes a piezoelectric element having a cylindrical shape with a longitudinal axis, an inner surface facing inwardly toward the longitudinal axis, and an outer surface facing outwardly away from the longitudinal axis; a plurality of external electrodes disposed on the outer surface of the piezoelectric element; and at least one internal electrode disposed on the inner surface of the piezoelectric element. The at least one internal electrode provides corresponding internal electrode portions that are disposed opposite the plurality of external electrodes with respect to the piezoelectric element, the external electrodes and the at least one internal electrode to be energized to apply an electric field across the piezoelectric element between the external electrodes and the corresponding internal electrode portions, so as to produce ultrasonic ablation zones extending from the energized external electrodes outwardly away from the longitudinal axis. The ultrasonic ablation zones of the external electrodes are distributed in a staggered configuration so as to span one or more open arc segments around the longitudinal axis, and the ultrasound ablation zones of all the external electrodes projected longitudinally onto any lateral plane which is perpendicular to the longitudinal axis span a substantially closed loop around the longitudinal axis.

In some embodiments, the external electrodes are discretely spaced from each other at least one of longitudinally or laterally, and at least two of the external electrodes are spaced from one another longitudinally. The external electrodes span one or more open arc segments around the longitudinal axis, but all the external electrodes projected longitudinally onto any lateral plane which is perpendicular to the longitudinal axis span a substantially closed loop around the longitudinal axis. The external electrodes and the at least one internal electrode are independently controlled to be energized in one of simultaneous manner, sequential manner, and arbitrary manner to produce the ultrasonic ablation zones. The external electrodes and the at least one internal electrode are energized by radiofrequency (RF) energy. The ablation apparatus further comprises a body having a fluid cavity in which the ultrasonic transducer is disposed, the fluid cavity containing a fluid for transmitting ultrasonic energy. The fluid cavity has a fluid inlet for fluid flow into the fluid cavity and a fluid outlet for fluid flow out of the fluid cavity.

In specific embodiments, the ablation apparatus further comprises a handle assembly; a shaft having a main lumen, a proximal end coupled to the handle assembly, and a distal end; a distal tip section coupled to the distal end of the shaft, the distal tip section having a non-compliant and non-porous cap that has a tubular wall that defines a bore; and an irrigation tube extending through the main lumen and having a distal end that terminates in the bore, the irrigation tube to supply irrigation fluid to the bore. The ultrasonic transducer is housed inside the bore and spaced apart from the wall of the cap. A plurality of thermocouple wires are connected to the cap. A plurality of ring electrodes are provided in a spaced-apart manner about the outer surface of the shaft adjacent the distal tip section. An inner sleeve is secured in the main lumen at the distal end of the shaft. An inner supporting member extends through the main lumen of the shaft and the bore of the cap.

In specific embodiments, the ablation apparatus further comprises a handle assembly; a shaft having a main lumen, a proximal end coupled to the handle assembly, and a distal end; an inner sleeve secured in the main lumen; a distal tip section coupled to the distal end of the shaft, the distal tip section having a non-compliant and non-porous cap that has a tubular wall that defines a bore; an inner supporting member that extends through the main lumen of the shaft and the bore of the cap; and an outer supporting member that extends through the inner sleeve and into the bore, with the inner supporting member housed in the outer supporting member. The ultrasonic transducer is housed inside the bore and spaced apart from the wall of the cap. The inner supporting member is selected from the group consisting of a coil, a flat wire, and made of a material selected from the group consisting of a metal, an alloy, and a polymer.

In specific embodiments, the ablation apparatus further comprises an expandable member providing a fluid cavity in which the ultrasonic transducer is disposed. The ablation apparatus further comprises a handle assembly; a shaft having a proximal end coupled to the handle assembly, and a distal end, the shaft extending along an axis; and a distal ring provided at the distal end and oriented perpendicular to the axis of the shaft, the distal ring having a plurality of electrodes positioned in spaced-apart manner about the distal ring. The ultrasonic transducer is positioned spaced apart from the distal ring. The distal ring has a diameter that is greater than the fully expanded diameter of the expandable member. The ablation apparatus further comprises an energy source coupled to the ultrasonic transducer; and means coupled to the plurality of electrodes for processing electrical signals received from the plurality of electrodes.

In accordance with another aspect of the invention, an ablation apparatus comprises a body have an axis and an ultrasonic transducer connected to the body, the ultrasonic transducer including a piezoelectric element coupled to the body, the piezoelectric element having a hollow interior, an inner surface facing the hollow interior, and an outer surface facing outwardly away from the hollow interior; a plurality of external electrodes disposed on the outer surface of the piezoelectric element; and at least one internal electrode disposed on the inner surface of the piezoelectric element. The at least one internal electrode provides corresponding internal electrode portions that correspond to the plurality of external electrodes, the external electrodes and the at least one internal electrode to be energized to apply an electric field across the piezoelectric element between the external electrodes and the corresponding internal electrode portions, so as to produce ultrasonic ablation zones extending from the energized external electrodes outwardly away from the hollow interior. The ultrasonic ablation zones of the external electrodes are distributed in a staggered configuration so as to span one or more open arc segments around the axis of the body, and the ultrasound ablation zones of all the external electrodes projected longitudinally onto any lateral plane which is perpendicular to the axis of the body span a substantially closed loop around the axis of the body.

In some embodiments, the external electrodes span one or more open arc segments around the axis of the body, but all the external electrodes projected longitudinally onto any lateral plane which is perpendicular to the axis of the body span a substantially closed loop around the axis of the body. The body has a fluid cavity in which the ultrasonic transducer is disposed, the fluid cavity containing a fluid for transmitting ultrasonic energy.

These and other features and advantages of the present invention will become apparent to those of ordinary skill in the art in view of the following detailed description of the specific embodiments.

BRIEF DESCRIPTION OF THE DRAWINGS

FIG. 6A is a simplified schematic view of the distal tip section of the catheter illustrating a modified cap according to another embodiment of the invention.

FIG. 7 illustrates a mapping and ablation system according to another embodiment of the present invention.

DETAILED DESCRIPTION OF THE INVENTION

Figure 1:
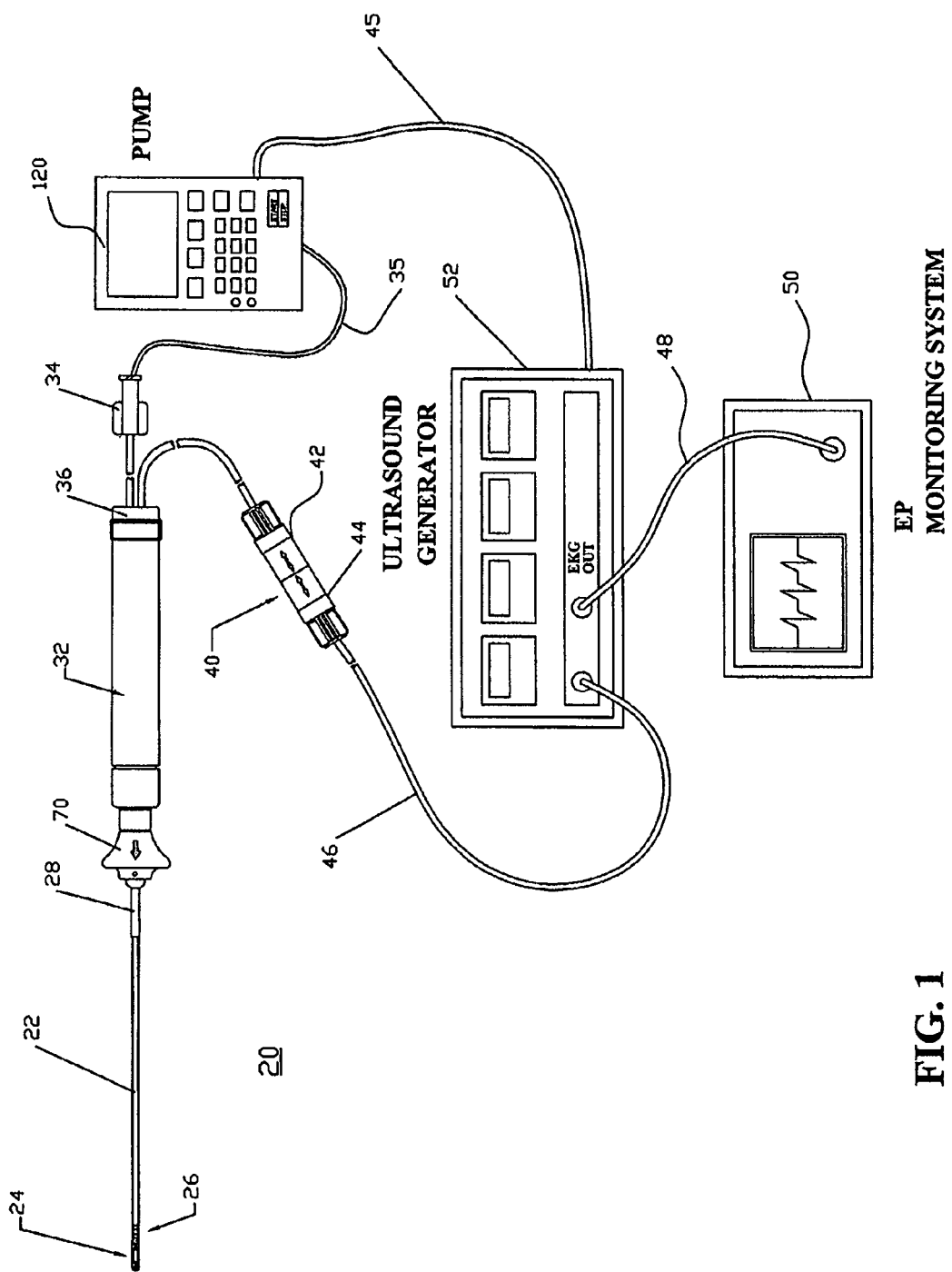
FIG. 1 illustrates a mapping and ablation system according to one embodiment of the present invention.
Figure 2:
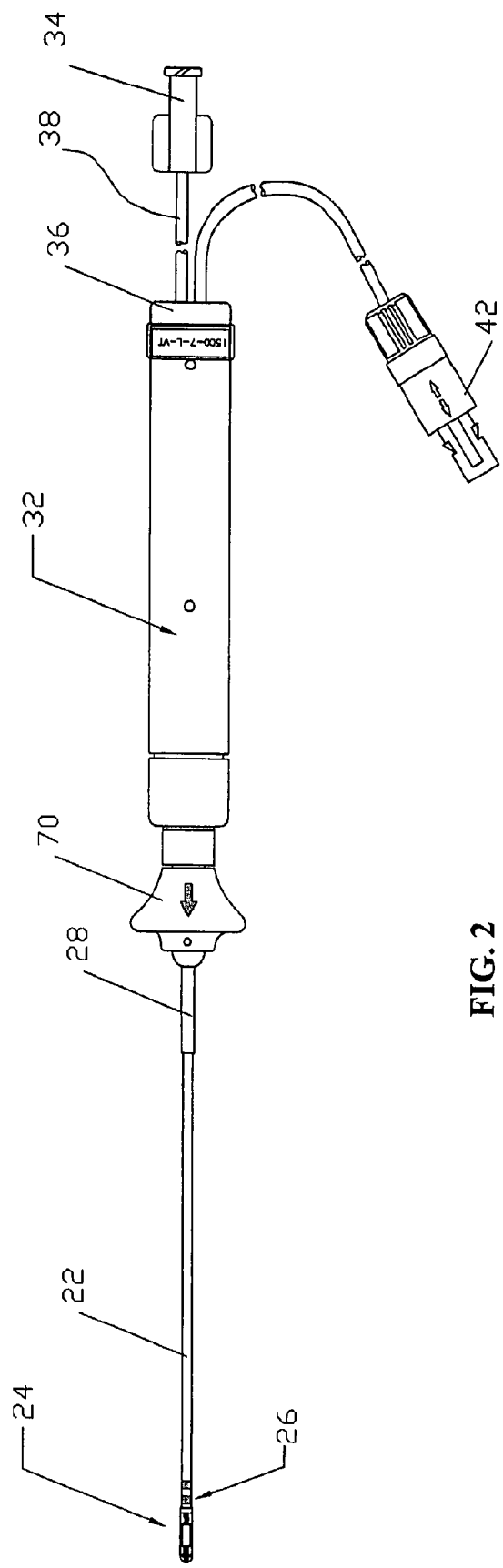
FIG. 2 is a side plan view of the catheter of the system of FIG. 1.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide assemblies of staggered ablation elements that are particularly suitable for renal denervation with a reduced risk of stenosis.

Noncontact Ablation Using Ultrasound

According to one embodiment of the invention, a catheter for ablating body tissue of the interior regions of the heart comprises a handle assembly; a shaft having a main lumen, a proximal end coupled to the handle assembly, and a distal end; a distal tip section coupled to the distal end of the shaft, the distal tip section having a non-compliant and non-porous cap that has a tubular wall that defines a bore; and an ablation element that is housed inside the bore and spaced apart from the wall of the cap. The ablation element produces acoustic energy. An irrigation tube extends through the main lumen and has a distal end that terminates in the bore.

FIGS. 1-6 illustrate a catheter system 20 according to this embodiment of the present invention. The catheter system 20 has a tubular shaft 22 having a distal end 26, a proximal end 28, and a main lumen 30 extending through the shaft 22. A distal tip section 24 is secured to the distal end 26 of the shaft 22. A handle assembly 32 is attached to the proximal end 28 of the shaft 22 using techniques that are well-known in the catheter art.

The distal tip section 24 has an ablation element 60 that is housed inside a non-compliant and non-porous tubular cap 62. The ablation element 60 is spaced from, and does not contact, the walls of the cap 62. The cap 62 has a bore 64 extending therethrough. The distal end 26 of the shaft 22 is slide-fitted into the bore 64 at the proximal end 66 of the cap 62, and secured to the cap 62 by adhesive bonding. An inner sleeve 68 is secured by adhesive bonding in the main lumen 30 at the distal end 26 of the shaft 22. The inner sleeve 68 is made of a plastic material such as PEEK and has multiple channels 67 (see FIG. 6) separating the wires, an inner supporting member 102, and a fluid lumen so they do not interfere with each other inside the cap 62 when the catheter is subjected to mechanical forces during use, including deflection of the distal tip, torque, and advancement and withdrawal from the patient. The cap 62 can be made from a non-compliant material such as polyethylene, polyurethane, polyolefins, polymethylpentene, and the like, that is capable of allowing ultrasound energy to be transmitted therethrough. The cap 62 extends from its proximal end 66 and terminates at a closed distal tip 92 that has an opening 94 provided thereat.

The ablation element 60 can be embodied in the form of a transducer or an electrode that includes a piezoelectric crystal which converts electrical energy into ultrasound energy. The transducer 60 is tubular, and O-rings 108 are positioned between the transducer 60 and a tubular outer supporting member 104 to create an air space between the supporting member 104 and the transducer 60 to minimize transmission of ultrasound waves inside the transducer 60. A silicone adhesive 110 seals the ends of the transducer 60. Irrigation fluid fills the space between the transducer 60 and the cap 62, so that the ultrasound energy can be transmitted through the fluid and the cap 62 into the body tissue. The fluid acts to cool the transducer 60, and functions as a medium to transmit the ultrasound energy. Since the transducer 60 has a diameter that is smaller than the inner diameter of the cap 62, the transducer 60 does not contact the body tissue.

An irrigation tube 100 extends through the main lumen 30 of the shaft 22, and has a distal end that terminates inside the proximal end 66 of the cap 62, at a location proximal to the transducer 60. Irrigation fluid is introduced from a pump 120 via a standard infusion tube 35 and a luer fitting 34 through the irrigation tube 100 to be delivered inside the bore 64 of the cap 62 for cooling the transducer 60.

The inner supporting member 102 extends through the main lumen 30 of the shaft 22 and the bore 64 of the cap 62, terminating adjacent the opening 94 in the distal tip 92. The inner supporting member 102 functions to provide support to the catheter shaft 22 and the distal tip section 24, and is received inside the outer supporting member 104 that extends through the inner sleeve 68 and into the bore 64. The inner supporting member 102 can be provided in the form of a coil, a flat wire, or a rod composed of metal, alloy or a polymer.

A plurality of thermocouple wires 54 can have their distal tips secured to the inner surface of the cap 62, and are used to detect the temperature at the ablation site.

A plurality of ring electrodes 58 are provided in spaced-apart manner about the outer surface of the shaft 22 adjacent the distal tip section 24. The ring electrodes 58 can be made of a solid, electrically conducting material, such as platinum-iridium, stainless steel, or gold, and are attached about the shaft 22. Alternatively, the ring electrodes 58 can be formed by coating the exterior surface of the shaft 22 with an electrically conducting material, such as platinum-iridium or gold. The coating can be applied by sputtering, ion beam deposition or similar known techniques. The number of ring electrodes 58 can vary depending on the particular geometry of the region of use and the functionality desired.

As will be explained in greater detail below, the ring electrodes 58 function to map the region of the heart that is to be treated. After the mapping has been completed, the transducer 60 is positioned at the location where ablation is to be performed, and the irrigation fluid through the lumen tube 100 is increased to the desired flow rate set on the pump 120. The flow of the irrigation fluid is software-controlled and its instructions are transmitted from the generator 52 to the pump 120 through the cable 45. The ablation is then carried out by energy that is emitted from the transducer 60 through the irrigation media (e.g., fluid, saline, contrast media or mixture) inside the cap 62.

A standard luer fitting 34 is connected to the proximal end of the tubing 38 extending out from the proximal end 36 of the handle assembly 32 using techniques that are well-known in the catheter art. The luer fitting 34 provides a fluid line for irrigation media to be introduced to cool the transducer 60 at the distal tip section 24 of the shaft 22. The irrigation media is delivered via the infusion tube 35 and into the irrigation tube 100 that extends from the luer fitting 34, and terminates in the bore 64 of the cap 62. The irrigation media exits from the holes 98 located distally of the transducer 60 at the distal end of the cap 62. In another embodiment, the cap 62 is completely closed without the distally located holes 98, and the irrigation media entering the bore 64 is withdrawn back out through another lumen tube (not shown) towards the proximal end of the catheter.

A connector assembly 40 is also connected to the proximal end 36 of the handle assembly 32 using techniques that are well-known in the catheter art. The connector assembly 40 has a proximal connector 42 that couples the handle assembly 32 to the connector 44 of a cable 46 that leads to an ultrasound generator 52. An EP monitoring system 50 is coupled to the ultrasound generator 52 via another cable 48. The EP monitoring system 50 can be a conventional EP monitor which receives (via the ultrasound generator 52) electrical signals detected by the electrodes 58, and processes and displays these intracardiac signals to assist the physician in locating the arrhythmogenic sites or pathways. The ultrasound generator 52 can be a conventional ultrasound generator that creates and transmits ablating energy to the transducer 60, which emits the acoustic energy to ablate the tissue that extends radially from the position of the cap 62.

Conductor wires 51 extend from the ultrasound generator 52 along the cables 46 and 48 (through the connector assembly 40, the handle assembly 32 and the lumen 30 of the shaft 22) to the distal tip section 24, where the conductor wires 51 couple the ring electrodes 58. The thermocouple wires 54 couple the cap 62, and the ultrasound wires 55 couple the transducer 60. The thermocouple wires 54 and ultrasound wires 55 can extend from the cap 62 and transducer 60 through the channels 67 of the inner sleeve 68 and through the lumen 30 of the shaft 22 and the handle assembly 32 to the proximal connector 42, where they can be electrically coupled by the internal thermocouple wires in the cable 46 to the ultrasound generator 52 where the temperature can be displayed.

Figure 3:
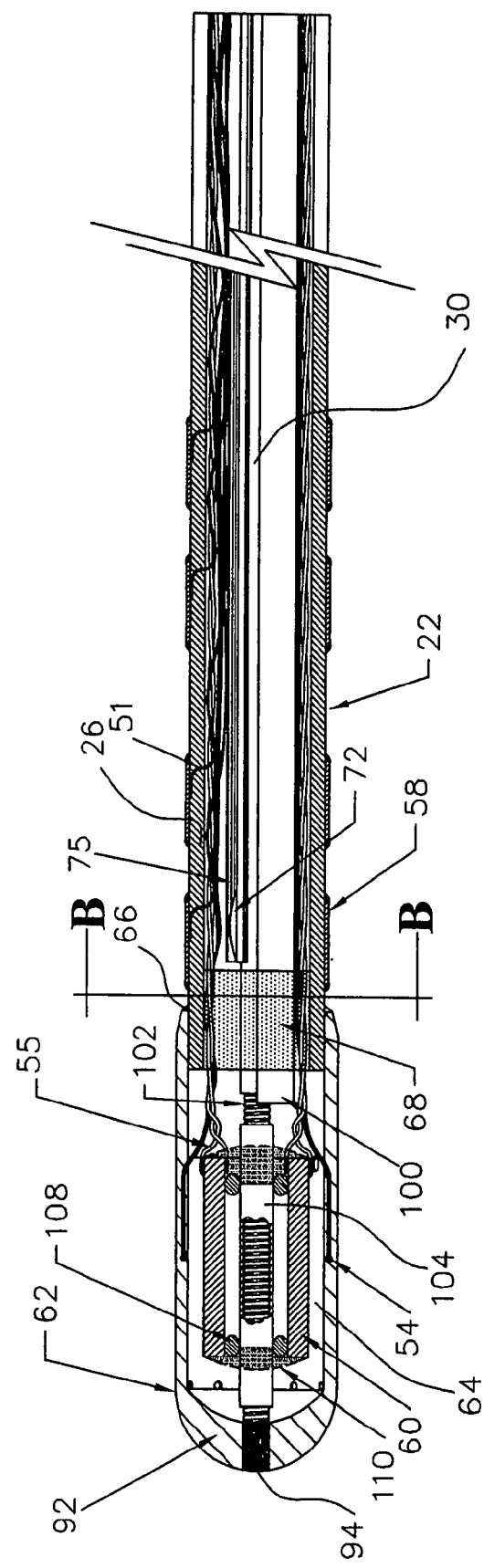
FIG. 3 is an enlarged cross-sectional view of the distal tip section of the catheter of FIGS. 1 and 2.
Figure 4:
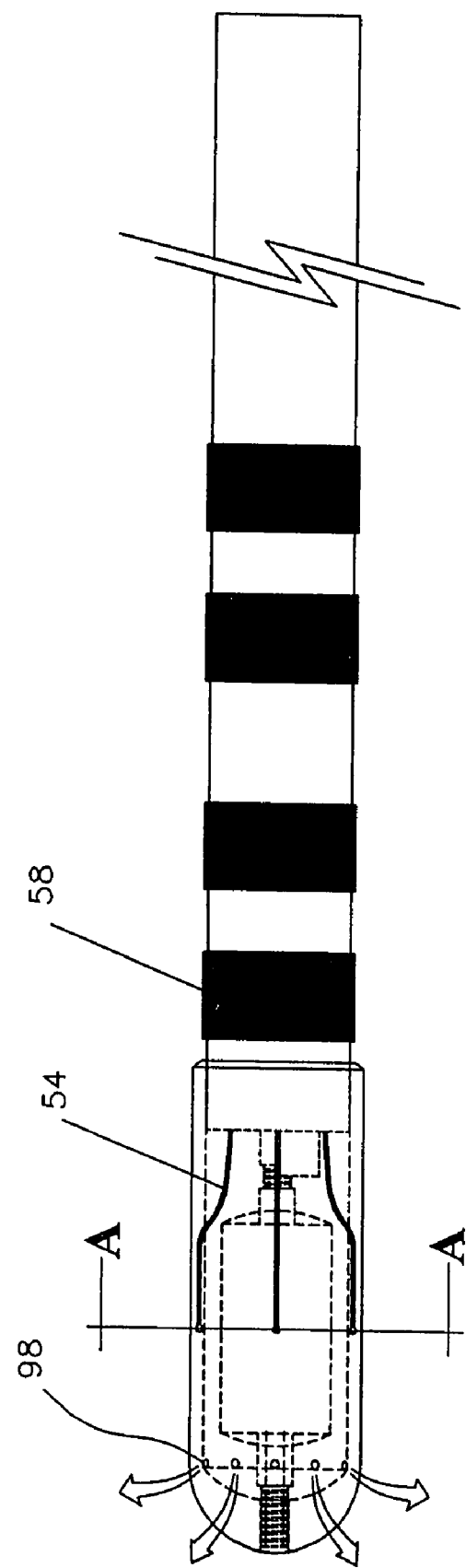
FIG. 4 is an enlarged side plan view of the distal tip section of the catheter of FIGS. 1 and 2.
Figure 5:
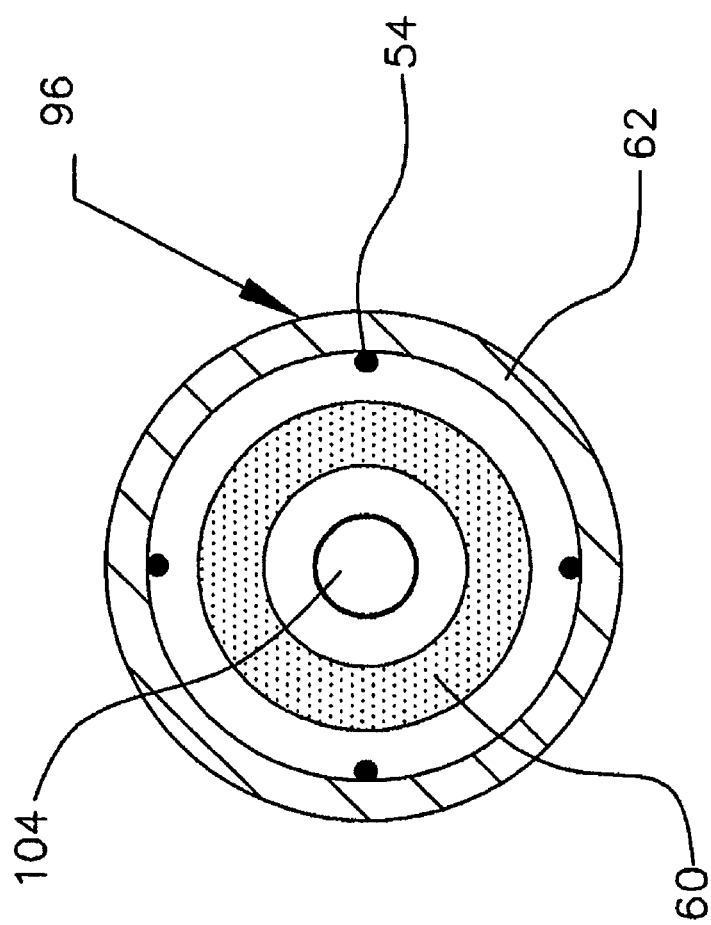
FIG. 5 is a cross-sectional view of the distal tip section of FIG. 4 taken along lines A-A thereof.
Figure 6:
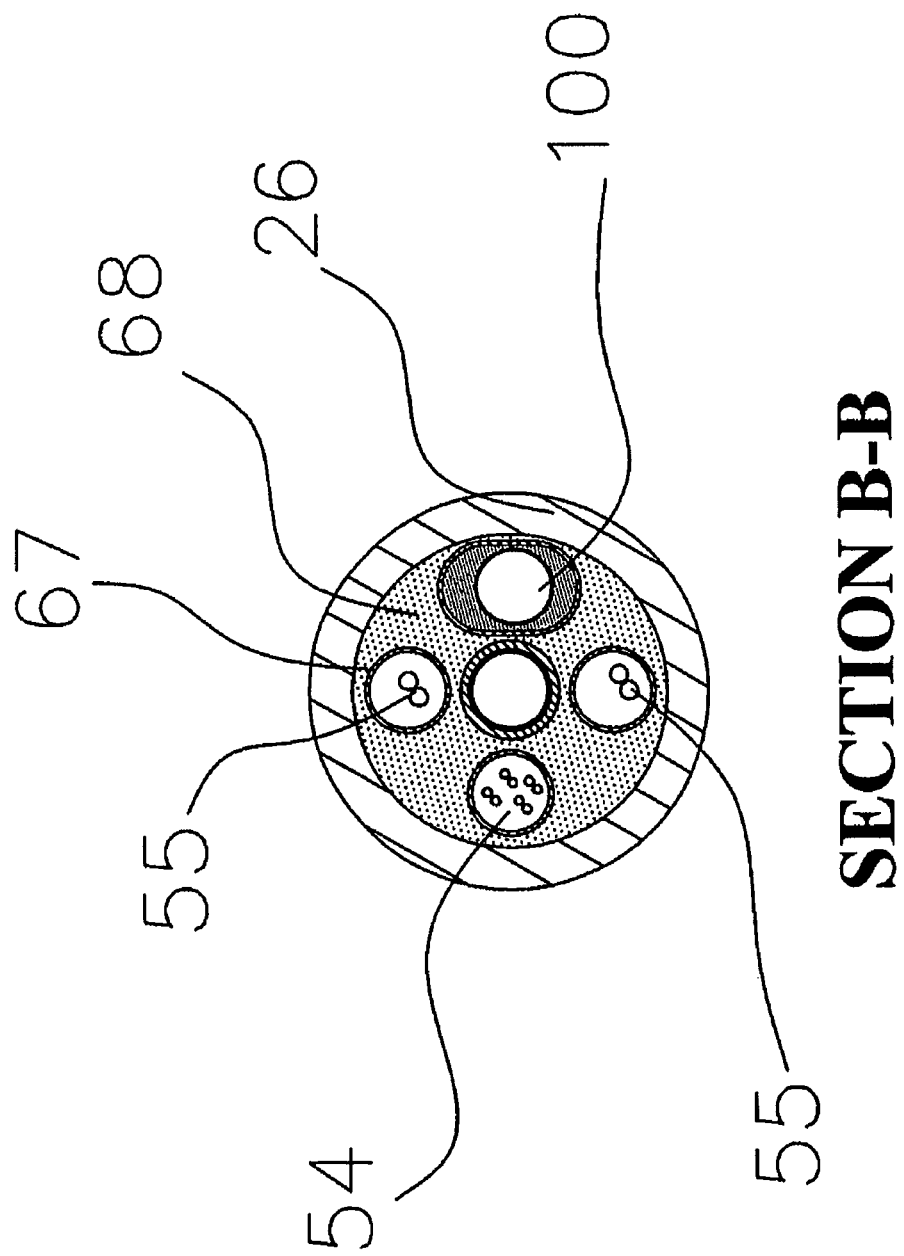
FIG. 6 is a cross-sectional view of the distal tip section of FIG. 3 taken along lines B-B thereof.
Figure 8:
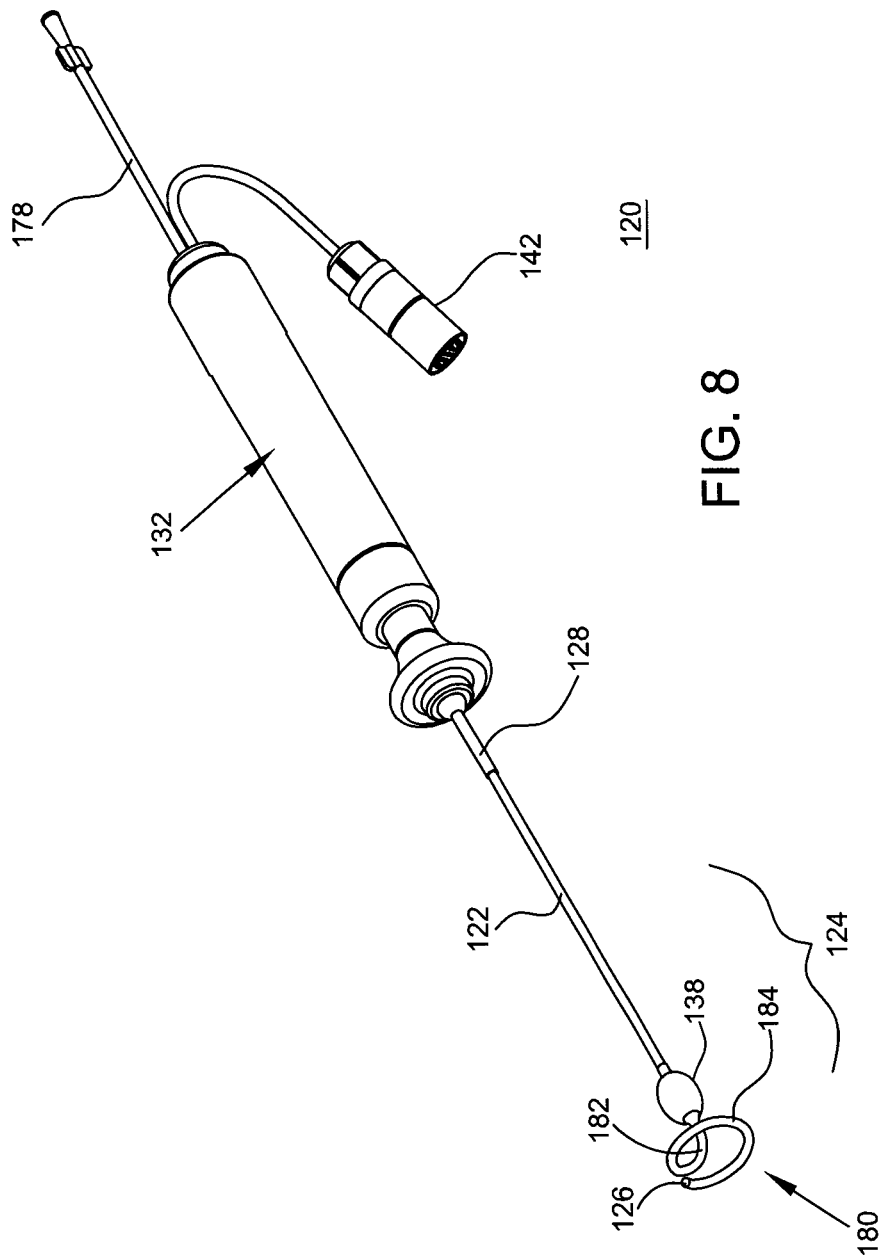
FIG. 8 is a perspective view of the catheter of the system of FIG. 7.

The handle assembly 32 also includes a steering mechanism 70 that functions to deflect the distal tip section 24 of the shaft 22 for maneuvering and positioning the distal tip section 24 at the desired location in the heart. Referring to FIG. 3, the steering mechanism 70 includes a steering wire 72 that extends in the main lumen 30 of the shaft 22 from its proximal end at the handle assembly 32 to its distal end which terminates at the distal end 26 of the shaft 22 before the location of the distal tip section 24. The distal end of the steering wire 72 is secured to a flat wire 75 that is fixedly positioned inside the handle assembly 32. The flat wire 75 extends in the lumen 30 from the anchor to its distal end at a location slightly proximal to the inner sleeve 68. The flat wire 75 is attached to the steering wire 72 at the distal ends of the flat wire 75 and the steering wire 72 so as to be controlled by the steering wire 72. Specifically, by pushing the steering mechanism 70 forward in a distal direction, the steering mechanism 70 will pull the steering wire 72 in a proximal direction, causing the distal tip section 24 to deflect to one direction. By pulling back the steering mechanism 70 in a proximal direction, the steering wire 72 is deactivated and the distal tip section 24 returns to its neutral position or deflects to the opposite direction for bi-directionality.

The operation and use of the catheter system 20 will now be described. To introduce and deploy the distal tip section 24 within the heart, the physician uses a conventional introducer sheath to establish access to a selected artery or vein. The physician introduces the shaft 22 through a conventional hemostasis valve on the introducer and progressively advances the catheter through the access vein or artery into the desired location within the heart. The physician observes the progress of the catheter using fluoroscopic or ultrasound imaging. The catheter can include a radio-opaque compound, such as barium sulfate, for this purpose. Alternatively, radio-opaque markers can be placed at the distal end of the introducer sheath.

The shaft 22 and the introducer sheath can be maneuvered to the left or right atrium or ventricle by the steering mechanism 70. Once located in the target location, good contact is established when the ring electrodes 58 contact the target endocardial tissue, and the intracardiac signals of the selected region are recorded through the ring electrodes 58. The results of the mapping operation are processed and displayed at the EP monitoring system 50. A differential input amplifier (not shown) in the EP monitoring system 50 processes the electrical signals received from the ring electrodes 58 via the wires 51, and converts them to graphic images that can be displayed. The thermocouple wires 54 can also function to monitor the temperature of the surrounding tissue, and provide temperature information to the ultrasound generator 52.

Once the desired position of the transducer 60 has been confirmed by mapping through the ring electrodes 58, and visually through fluoroscopy, the physician can then increase the irrigation fluid flow rate by turning the power of the ultrasound generator 52 on which controls the fluid flow rate prior to the start of ablation. The ultrasound generator 52 delivers high frequency energy that is propagated through the wires 55 to the ultrasound transducer 60 that is positioned inside the cap 62. The acoustic energy radiates in a radial manner from the transducer 60, propagates through the irrigation media (which acts as an energy transmitting medium), exits the cap 62 and then reaches the selected tissue (typically in a pressure waveform) to ablate the tissue.

In another embodiment with a modified cap 62a as shown in FIG. 6A, the acoustic energy after exiting the cap 62a propagates through the blood in the blood vessel 63 and then reaches the tissue. The balloon 65 serves to center the transducer within the blood vessel 63.

Ultrasound Ablation Using Expandable Member

Another embodiment of the invention is directed to a catheter for sensing electrical events about a selected annulus region of the heart and for treating tissue in the selected annulus region. The catheter comprises a handle assembly; a shaft having a proximal end coupled to the handle assembly, and a distal end, the shaft extending along an axis; a distal ring provided at the distal end and oriented perpendicular to the axis of the shaft, the distal ring having a plurality of electrodes positioned in spaced-apart manner about the distal ring; an ablation element positioned spaced apart from the distal ring an expandable member covering the ablation element; and wherein the distal ring has a diameter that is greater than the fully expanded diameter of the expandable member. The ablation element inside the expandable member includes an ultrasound transducer.

FIGS. 7-14 illustrate a catheter system 120 according to this embodiment of the present invention. The catheter system 120 has a tubular shaft 122 having a distal tip section 124, a distal end 126, a proximal end 128, and at least one lumen 130 extending through the shaft 122. A handle assembly 132 is attached to the proximal end 128 of the shaft 122 using techniques that are well-known in the catheter art.

The distal tip section 124 includes an expandable balloon 138 and a distal ring 180 that makes up the distal-most end of the shaft 122. A transducer 160 (e.g., piezoelectric or ultrasound) is housed inside the balloon 138. The balloon 138 can be made from any conventional material (such as but not limited to silicone, polyurethane, latex, polyamide and polyethylene), and heat bonded or otherwise attached to the shaft 122 using techniques that are well-known in the catheter art.

The distal ring 180 can be preformed into a generally curved or circular shape, resembling an open arc segment. The shape of the distal ring 180 corresponds to the circumferential geometry of a selected annulus (e.g., the PV) in the heart. In fact, the preformed shape of the distal ring 180 can be provided in a variety of curved geometries to overlie the anatomical geometry of the selected annulus. The distal ring 180 includes a transition section 182 that extends distally at an angle from the longitudinal axis of the shaft 122, and has a generally open-looped circular section 184 that extends from the transition section 182. As best seen from FIG. 9, the circular section 184 is oriented at an approximately perpendicular orientation from the longitudinal orientation of the shaft 122. The distal ring 180 can be made from the same material as the shaft 122. Such a material can be an electrically nonconductive, biocompatible, resilient plastic material which retains its shape and which does not soften significantly at human body temperature (e.g., Pebax™, polyethylene or polyester). As a non-limiting example, the geometry of the distal ring 180 can be created by thermoforming it into the desired shape.

A plurality of thermocouple wires 154 can have their distal tips secured to the interior surface of the balloon 138 (see FIG. 9), and are used to detect the temperature at the treatment site.

A plurality of ring electrodes 158 are provided in spaced-apart manner about the circular section 184 of the distal ring 180. The ring electrodes 158 can be made of a solid, electrically conducting material, such as platinum or gold, and are attached about the circular section 184. Alternatively, the ring electrodes 158 can be formed by coating the exterior surface of the circular section 184 with an electrically conducting material, such as platinum or gold. The coating can be applied by sputtering, ion beam deposition or similar known techniques. The number of ring electrodes 158 can vary depending on the particular geometry of the region of use and the functionality desired.

As will be explained in greater detail below, the ring electrodes 158 function to map the region of the heart that is to be treated. After the mapping has been completed, the balloon 138 is positioned at the location where ablation is to be performed, and the distal ring 180 functions to anchor the position of the balloon 138. The balloon 138 is expanded, but even the greatest expanded diameter of the balloon 138 will be provided to be less than the diameter of the distal ring 180 when the distal ring 180 is fully deployed (see FIGS. 8, 9, and 13). The ablation is then carried out by energy that is emitted from the ultrasound transducer 160 through the inflation media (e.g., fluid, saline, contrast media or mixture) inside the balloon 138, and the balloon 138 itself.

A standard Luer fitting 134 is connected to the proximal end 136 of the handle assembly 132 using techniques that are well-known in the catheter art. The Luer fitting 134 provides a fluid line for inflation media to be introduced to inflate the balloon 138 at the distal tip section 124 of the shaft 122. The inflation media is delivered via an inflation lumen 176 that extends from the handle assembly 132 (and coupled to the line 178 of the Luer fitting 134), and terminates at the balloon 138.

A connector assembly 140 is also connected to the proximal end 136 of the handle assembly 132 using techniques that are well-known in the catheter art. The connector assembly 140 has a proximal connector 142 that couples the handle assembly 132 to the connector 144 of a control line 146 that leads to an ultrasound generator 152. An EP recording system 150 is coupled to the ultrasound generator 152 via another line 148. The EP recording system 150 can be a conventional EP monitor which receives (via the ultrasound generator 152)

electrical signals detected by the ring electrodes 158 at the distal tip section 124, and processes and displays these electrical signals to assist the physician in locating the site of potentials in a PV. The ultrasound generator 152 can be a conventional ultrasound generator that creates and transmits ablating energy to the ultrasound transducer 160 that is positioned inside the balloon 138. The ultrasound transducer 160 will emit the energy to ablate the tissue that extends radially from the position of the balloon 138.

Electrical wires (not shown) extend from the ultrasound generator 152 along the lines 146 and 148, and conductor wires 162 and ultrasound wires 163 extend through the connector assembly 140, the handle assembly 132 and the lumen 130 of the shaft 122 to the distal tip section 124 of the shaft 122 to couple the ring electrodes 158 and the transducer 160, respectively. In addition, the thermocouple wires 154 can extend from the balloon 138 through the lumen 130 of the shaft 122 and the handle assembly 132 to the proximal connector 142, where they can be electrically coupled by the wires in the line 146 to the ultrasound generator 152 where the temperature can be displayed.

Figure 11:
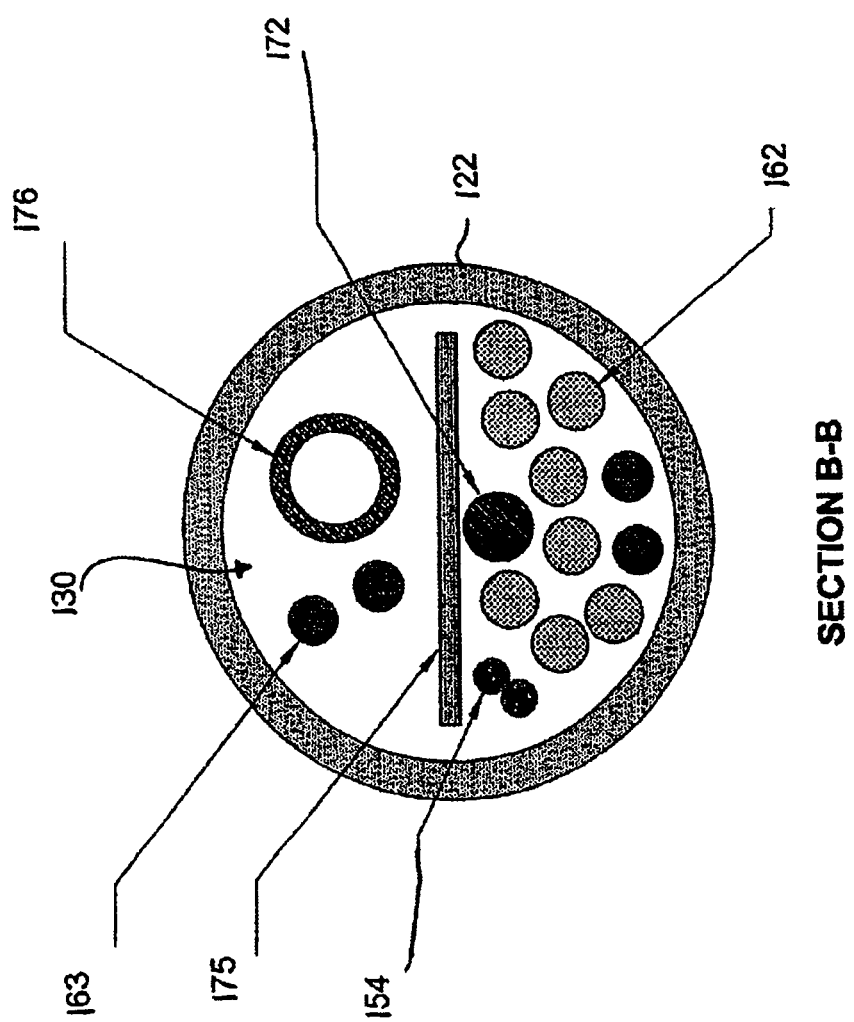
FIG. 11 is a cross-sectional view of the distal tip section of FIG. 9 taken along lines B-B thereof.
Figure 14:
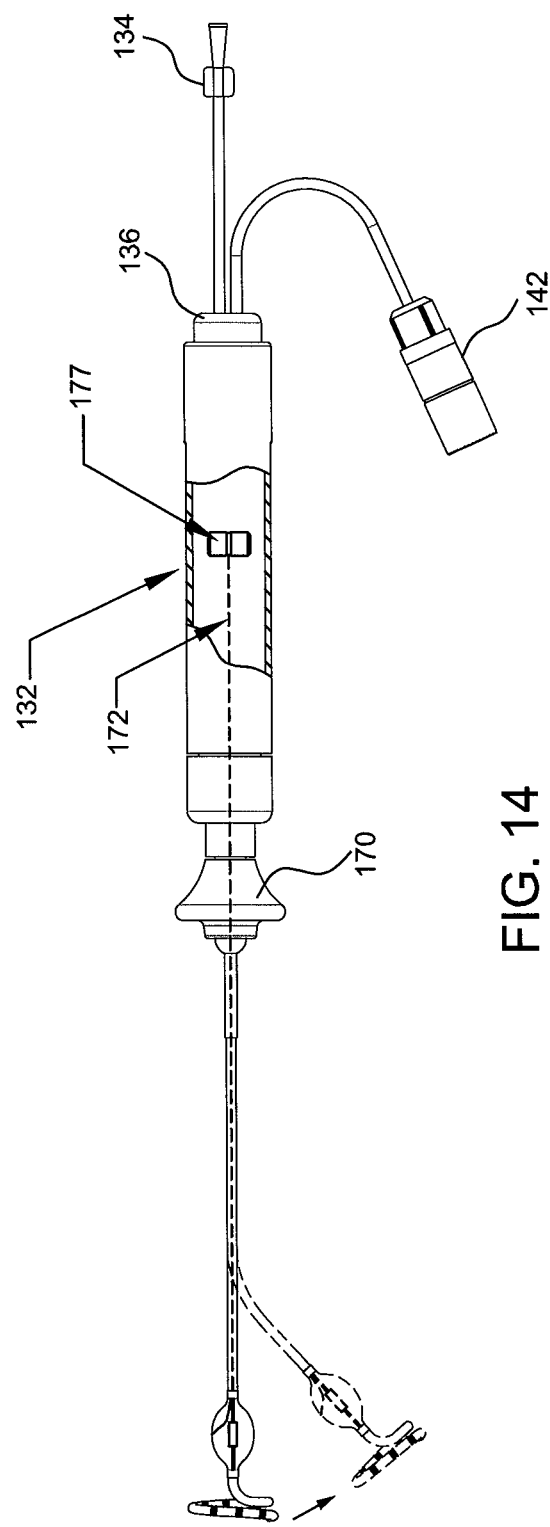
FIG. 14 illustrates the steering mechanism of the catheter of FIGS. 7 and 8.

The handle assembly 132 also includes a steering mechanism 170 that functions to deflect the distal tip section 124 of the shaft 122 for maneuvering and positioning the distal tip section 124 at the desired location in the heart. Referring to FIGS. 7, 11, and 14, the steering mechanism 170 includes a steering wire 172 that extends in the main lumen 130 of the shaft 122 from its proximal end at the handle assembly 132 to its distal end which terminates in the distal tip section 124 before the location of the balloon 138. The proximal end of the steering wire 172 is wound around or secured to an anchor 177 that is fixedly positioned inside the handle assembly 132. The steering mechanism 170 also includes a flat wire 175 that extends in the lumen 130 from the anchor 177 to its distal end at a location slightly proximal to the balloon 138 (as shown in FIG. 11). The flat wire 175 is attached to the steering wire 172 at the distal ends of the flat wire 175 and the steering wire 172 so as to be controlled by the steering wire 172. Specifically, by pushing the steering mechanism 170 forward in a distal direction, the steering mechanism 170 will pull the steering wire 172 in a proximal direction, causing the distal tip section 124 to deflect to one direction (see in phantom in FIG. 14). By pulling back the steering mechanism 170 in a proximal direction, the steering wire 172 is deactivated and the distal tip section 124 returns to its neutral position or deflects to the opposite direction.

The distal ring 180 can be preformed to a fixed size (i.e., diameter) and shape that cannot be changed. Alternatively, the diameter of the distal ring 180 can be adjusted using techniques and incorporating mechanisms that are well-known in the catheter art.

Figure 12:
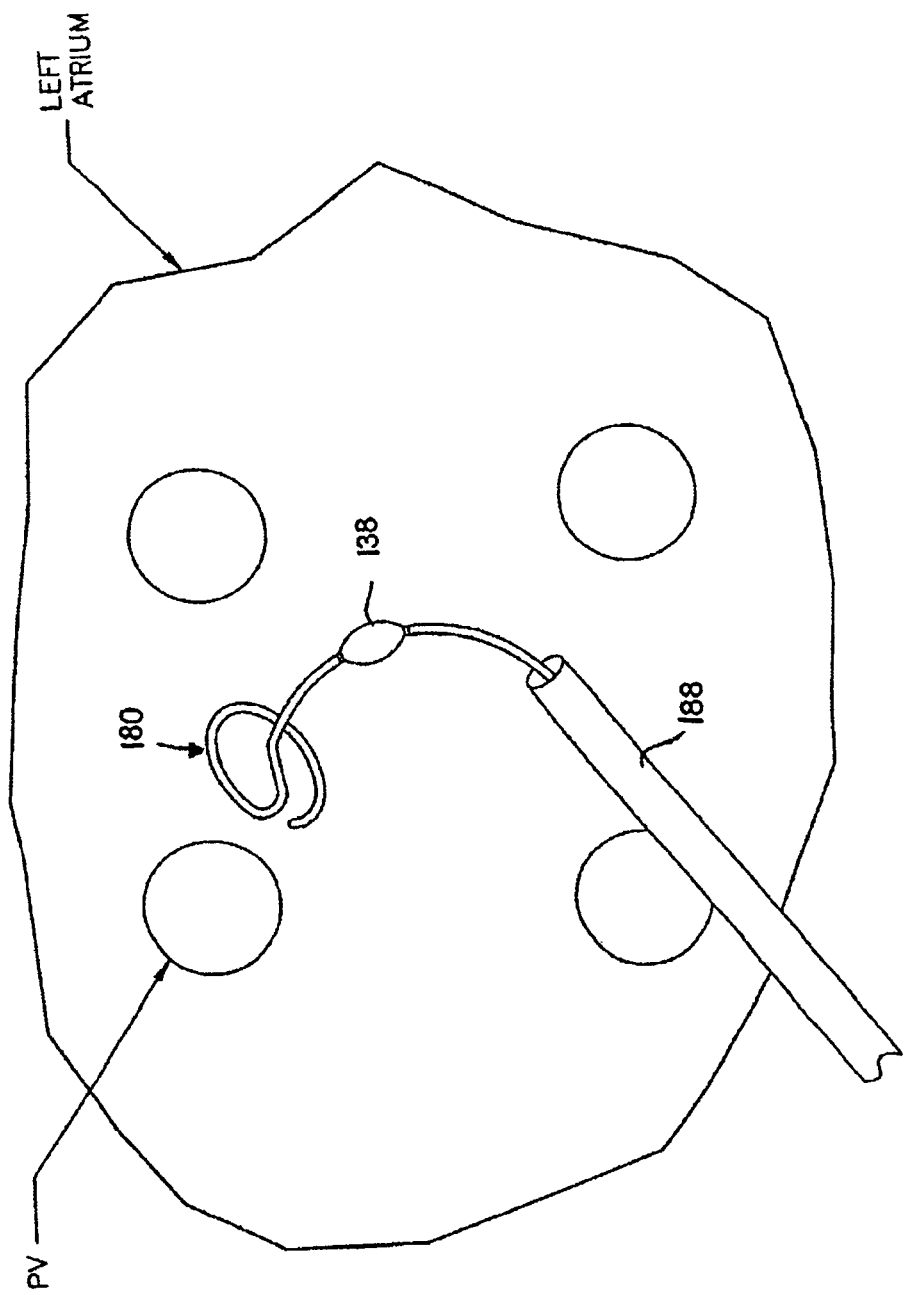
FIG. 12 illustrates how the catheter of FIGS. 7 and 8 is deployed for use inside the heart of a patient.
Figure 13:
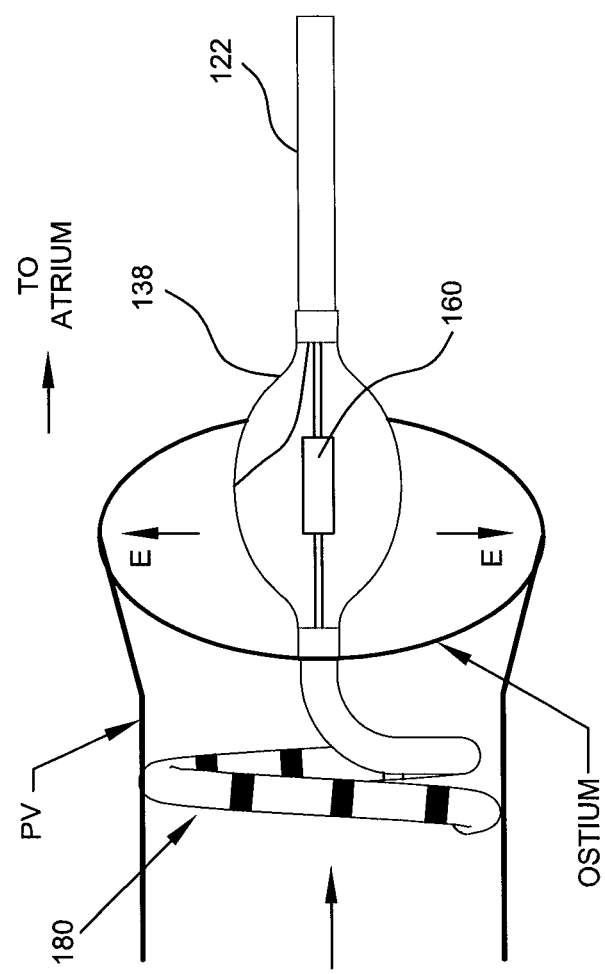
FIG. 13 is a cross-sectional view illustrating the catheter of FIGS. 7 and 8 in use in a pulmonary vein during the mapping and ablation steps.

FIGS. 12 and 13 illustrate how the catheter system 120 is used. First, a guide sheath 188 is provided to deliver the shaft 122 and distal ring 180 to the desired location (e.g., the left atrium) in the heart. The shaft 122 is slid into the hollow lumen of the guide sheath 188, and the guide sheath 188 can slide forward and backward along the longitudinal axis of the shaft 122. When the guide sheath 188 is slid forwardly towards the distal ring 180, the distal ring 180 is progressively straightened out and drawn into the lumen of the guide sheath 188. Thus, when confined with the guide sheath 188, the distal ring 180 assumes the generally linear low profile shape of the guide sheath 188, which allows a physician to employ conventional percutaneous access techniques to introduce the catheter 120 into a selected region of the heart through a vein or artery. When the guide sheath 188 is slid rearwardly away from the distal ring 180, the distal ring 180 is uncovered and its resilient memory will cause the distal ring 180 to re-assume its preformed generally circular shape.

To introduce and deploy the distal tip section 124 within the heart, the physician uses a conventional introducer to establish access to a selected artery or vein. With the guide sheath 188 confining the distal ring 180, and with the balloon 138 deflated, the physician introduces the shaft 122 and the guide sheath 188 through a conventional hemostatic valve on the introducer and progressively advances the guide sheath 188 through the access vein or artery into the desired atrium, such as the left atrium as shown in FIG. 12. The physician observes the progress of the guide sheath 188 using fluoroscopic or ultrasound imaging. The guide sheath 188 can include a radio-opaque compound, such as barium, for this purpose. Alternatively, radio-opaque markers can be placed at the distal end of the guide sheath 188.

The shaft 122 and the guide sheath 188 can be maneuvered to the left atrium by the steering mechanism 170. Once located in the left atrium, the physician slides the guide sheath 188 back to free the distal ring 180 which resiliently returns to its preformed shape. The distal ring 180 is then maneuvered into contact with the selected annulus (e.g., the ostium) with the aid of fluoroscopy. Good contact is established when the ring electrodes 158 contact the selected annulus, and at this time, the physician operates a control located on the ultrasound generator 152 to effectuate the mapping of the selected annulus by the ring electrodes 158. The results of the mapping operation are processed and displayed at the EP recording system 150. A differential input amplifier (not shown) in the EP recording system 150 processes the electrical signals received from the ring electrodes 158 via the wires 162, and converts them to graphic images that can be displayed. The thermocouple wires 154 can also function to monitor the temperature of the surrounding tissue, and provide temperature information to the ultrasound generator 152. Throughout this mapping operation, the balloon 138 remains deflated.

Once the mapping operation has been completed, the distal tip section 124 is maneuvered forward so that the balloon 138 can be positioned at the desired treatment location (e.g., the PV ostium in FIG. 13). Once the desired position of the balloon 138 has been confirmed, the physician can then inflate the balloon 138 using inflation media. The balloon 138 is preferably manufactured using known techniques to a predetermined diameter so that its diameter at its maximum expansion will be less than the diameter of the distal ring 180 and the annulus or vessel (e.g., the PV in FIG. 13) where the ablation is to take place. The physician then controls the ultrasound generator 152 to generate ultrasound energy that is propagated through the wires 163 to the ultrasound transducer 160 that is positioned inside the balloon 138. The energy radiates in a radial manner from the transducer 160, propagates through the inflation media (which acts as an energy transmitting medium) inside the balloon 138, exits the balloon 138 and then reaches the selected tissue (typically in a waveform) to ablate the tissue. See the arrows E in FIG. 13 which illustrate the radiation of the energy from the transducer 160.

During the ablation, the distal ring 180 functions to anchor the distal tip section 124 inside the PV at the desired location so that the ablation can be performed accurately. In contrast to known catheter systems where the same element is used to anchor and ablate, by providing a separate element (i.e., the distal ring 180) to anchor the distal tip section 124, the function of the ablation element (i.e., the balloon 138 and transducer 160) will not be affected by the anchoring device, thereby ensuring that the ablation is performed accurately and effectively. In addition, since the maximum diameter of the balloon 138 is always smaller than the smallest diameter of the distal ring 180, blood will be able flow through the distal ring 180 and around the surfaces of the balloon 138. When the ablation has been completed, the balloon 138 is deflated and the distal tip section 124 withdrawn from the heart.

Ultrasonic Ablation with Discrete Staggered Ablation Zones

Figure 9:
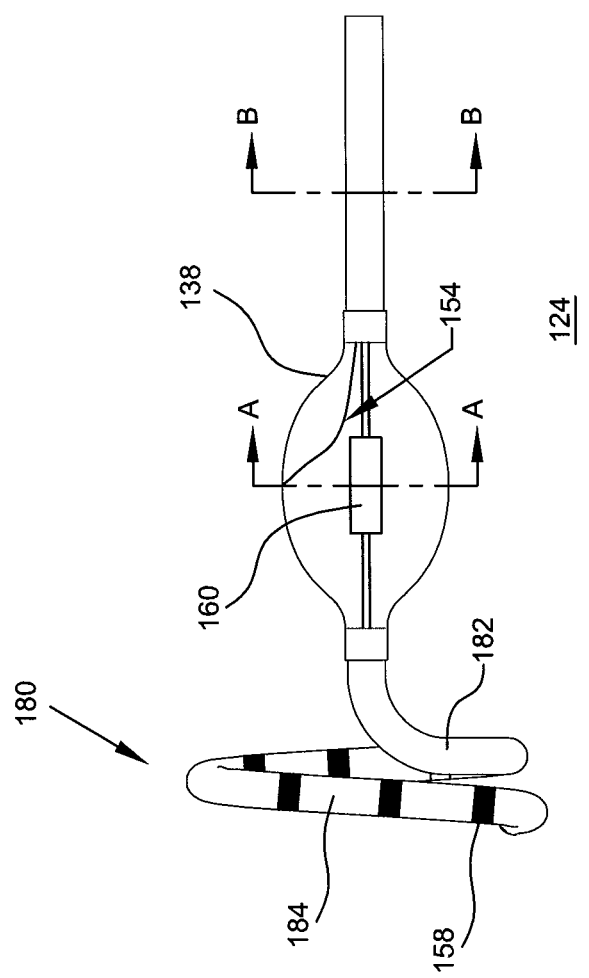
FIG. 9 is an enlarged view of the distal tip section of the catheter of FIGS. 7 and 8.
Figure 10:
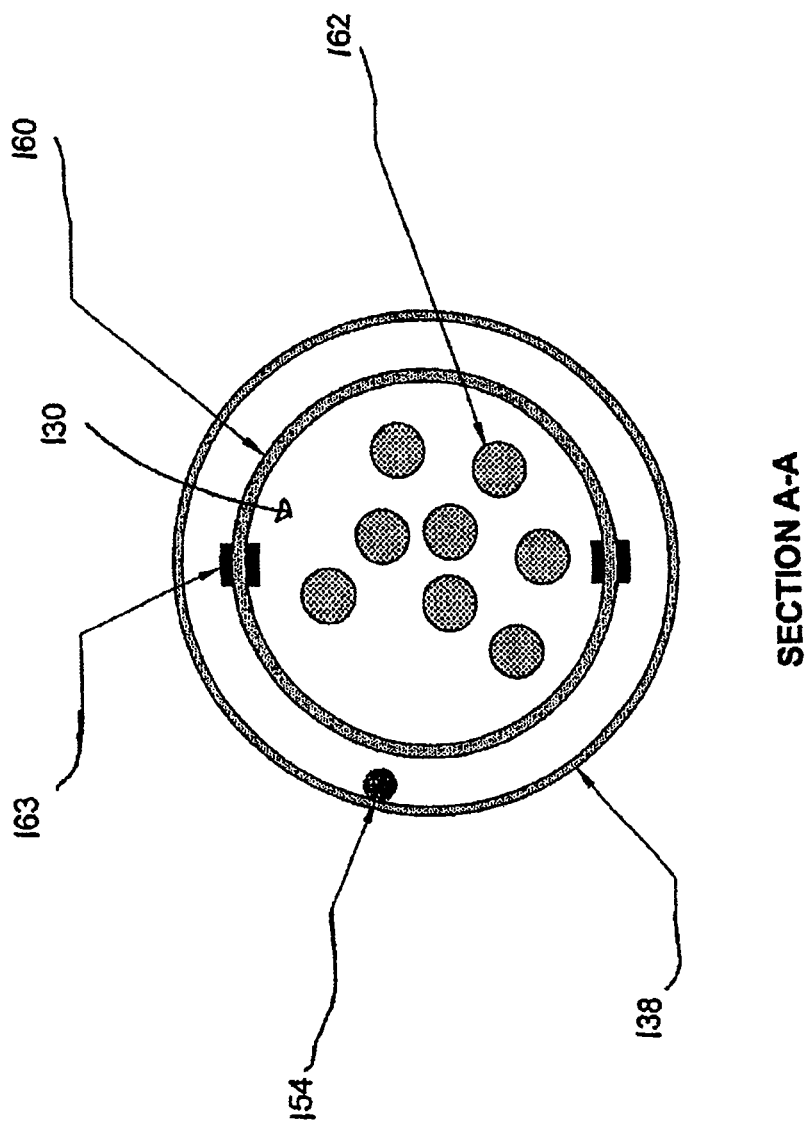
FIG. 10 is a cross-sectional view of the distal tip section of FIG. 9 taken along lines A-A thereof.

The ablation transducer 60 in FIG. 3 and the ablation transducer 160 in FIG. 9 emit ultrasonic energy around the circumference to produce ablation zones that form a substantially closed loop in the target tissue. For renal denervation, a closed loop ablation is not desirable due to the risk of renal artery/vein stenosis. According to the present invention, the ultrasonic transducer produces ablation zones that span one or more open arc segments around the longitudinal axis of the catheter, but all the ablation zones projected longitudinally onto any lateral plane which is perpendicular to the longitudinal axis span a substantially closed loop around the longitudinal axis. Because the ablation zones do not form a closed loop, the risk of renal artery/vein stenosis is reduced or eliminated. On the other hand, because the ablation zones of all the ablation elements projected longitudinally onto any lateral plane span a substantially closed loop, a complete renal denervation is achieved.

Piezoelectric ceramic and crystals are used in ultrasound transducers to transmit and receive ultrasound waves. A piezoelectric crystal changes the physical dimensions when subjected to an electric field. The piezoelectric crystal in ultrasound transducers has electrodes attached to its front and back for the application and detection of electrical charges. The crystal consists of numerous dipoles, and in the normal state, the individual dipoles have an oblique orientation with no net surface charge. In ultrasound physics, an electric field applied across the crystal will realign the dipoles and results in compression or expansion of the crystal, depending on the direction of the electric field. For the transmission of a short ultrasound pulse, a voltage spike of very short duration is applied, causing the crystal to initially contract and then vibrate for a short time with its resonant frequency.

Figure 15:
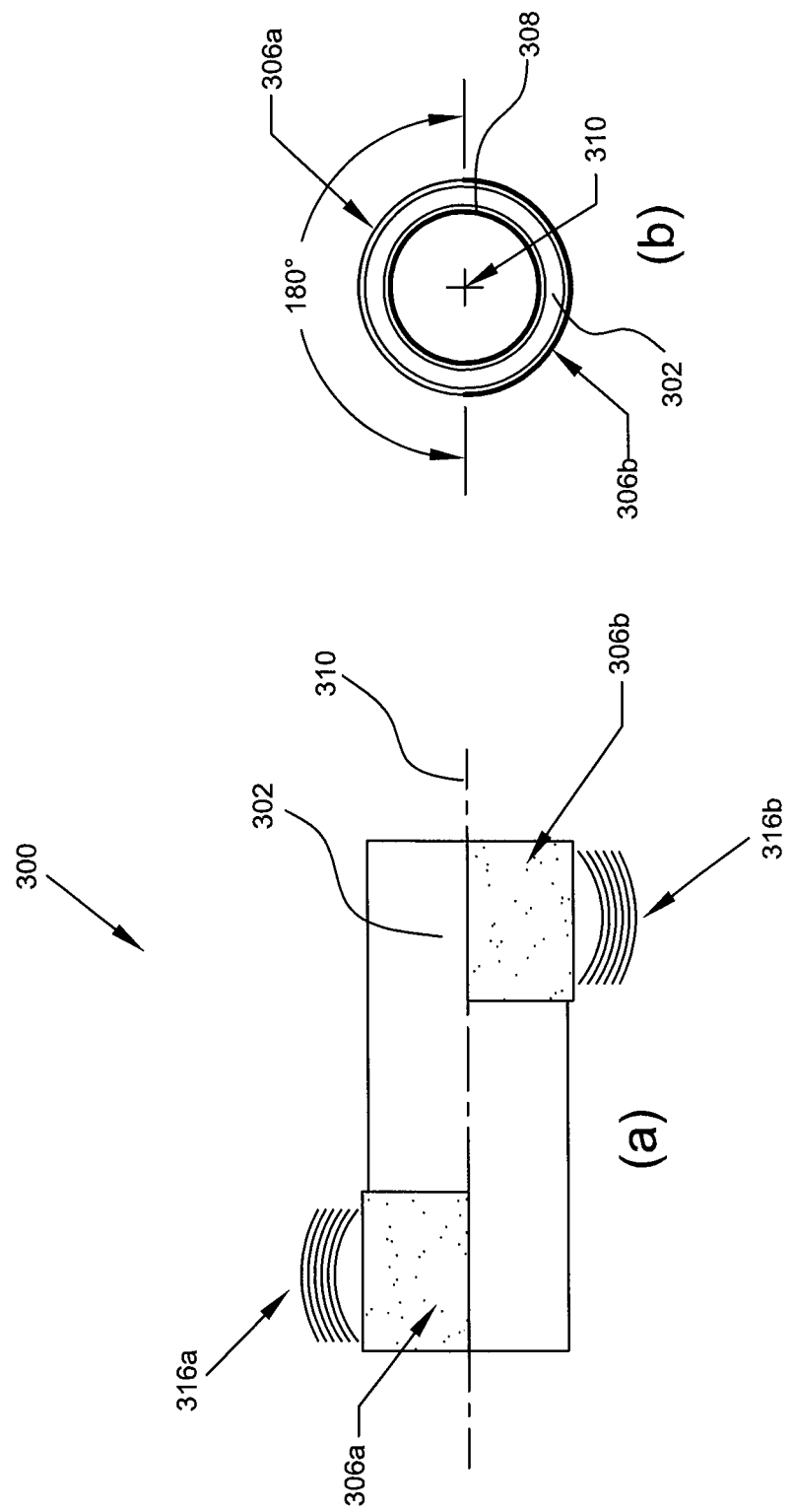
FIGS. 15(a) and 15(b) illustrate an ultrasonic transducer having electrodes arranged to produce discrete, staggered ablation zones.

FIG. 15 illustrates an ultrasonic transducer having electrodes arranged to produce discrete, staggered ablation zones. FIG. 15a is a front elevational view, and FIG. 15b is a side elevational view. The transducer has a hollow interior, an inner surface facing the hollow interior, and an outer surface facing outwardly away from the hollow interior, a plurality of external electrodes disposed on the outer surface of the piezoelectric element, and at least one internal electrode disposed on the inner surface of the piezoelectric element. In the embodiment shown, the transducer is cylindrical in shape, and includes internal and external electrodes with a piezoelectric elements sandwiched therebetween. Instead of having internal and external electrodes that each extend around the circumference of the transducer, discrete electrodes are used to provide sector ablation, forming a plurality of discrete ablation zones.

In FIG. 15, the transducer 300 includes a piezoelectric element 302 having on its outer surface a plurality of external electrodes 306a, 306b. The transducer 300 may have a plurality of corresponding internal electrodes that correspond to the external electrodes 306a, 306b (each pair of corresponding internal electrode and external electrode being disposed generally directly on opposite sides of the piezoelectric element 302). Alternatively, it may instead have a single internal electrode 308 on the inner surface of the piezoelectric element 302. The single internal electrode 308 covers an area sufficiently large to include internal electrode portions that correspond to the external electrodes 306a, 306b (each pair of corresponding internal electrode portion and external electrode being disposed generally directly on opposite sides of the piezoelectric element 302). In a specific embodiment, the single internal electrode 308 covers the entire inner surface of the piezoelectric element 302. Examples of materials for the piezoelectric element 302 include piezoceramics such as PZT (lead zirconate titanate). The electrodes 306a, 306b, 308 are metallic coatings or plates (e.g., nickel) formed on the inner and outer surfaces of the piezoelectric element 302. Each of the electrodes 306a, 306b, 308 is connected via a conductor wire to an energy source (e.g., electrical, RF, or the like). If there are independent energy sources, energy can be supplied to the electrodes independently. Otherwise, energy is supplied to the electrodes simultaneously.

The energy source is usually RF because it produces ultrasonic energy at a wavelength that is suitable for tissue ablation or nerve denervation. The ultrasonic energy is typically about 6.8 to 7.5 MHz. The transducer 300 is a thickness-mode transducer in specific embodiments. In one example, the piezoelectric element 302 has a nominal thickness of about 0.0115 inch. The electrodes 306a, 306b, 308 are even thinner, typically several microns (e.g., 4-5 microns).

FIG. 15 shows two discrete external electrodes 306a, 306b. They are generally semicircular, and are disposed on opposite sides of the cylindrical transducer 300 and longitudinally spaced from one another so as not to form a complete loop around the longitudinal axis 310 of the transducer 300. The longitudinal axis 310 of the transducer 300 is parallel to the longitudinal axis of the catheter and, typically, the two longitudinal axes coincide with one another. When energy is supplied to the electrodes 306, 308 with the piezoelectric element 302 sandwiched therebetween, ultrasonic energy is transmitted from the external electrodes 306a, 306b outwardly for sector ablation within the corresponding ablation zones 316a, 316b of the external electrodes 306a, 306b. The ultrasonic energy is carried by the irrigation fluid between the transducer 300 (replacing 60) and the cap 62 of FIG. 3, or by the fluid inside the balloon 138 of FIG. 9. Blood within the patient's body in which the transducer 300 is disposed may also carry the ultrasonic energy to the target tissue or nerve.

The arrangement of the external electrodes 306a, 306b produces the staggered ablation zones 316a, 316b that span open arc segments around the longitudinal axis 310 of the transducer 300. Each ablation zone is a region that is energized with sufficient energy to ablate tissue or denervate nerves within the ablation zone. The two staggered, generally semi-circular external electrodes 306a, 306b produce the ablation zones 316a, 316b that form open arc segments around the longitudinal axis 310. The two external electrodes 306a, 306b may extend beyond 180°, so long as they produce ablation zones that do not form a closed loop. In other embodiments, there may be three or more external electrodes of other shapes.

Figure 16:
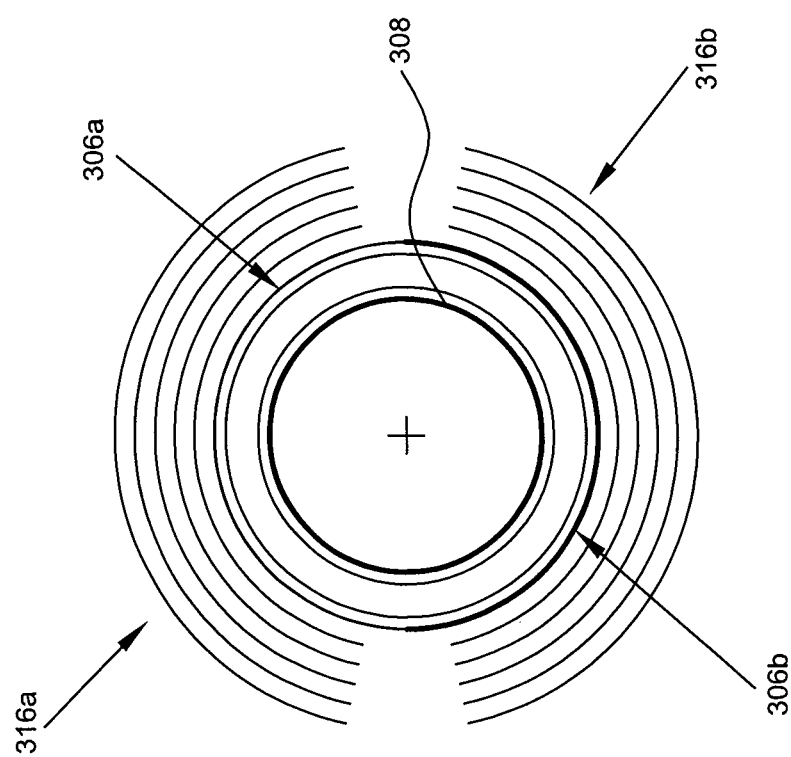
FIG. 16 illustrates the ablation zones of all the external electrodes that, when projected longitudinally onto any lateral plane which is perpendicular to the longitudinal axis, span a closed loop around the longitudinal axis of the transducer.

FIG. 16 illustrates the ablation zones 316a, 316b of all the external electrodes 306a, 306b that, when projected longitudinally onto any lateral plane which is perpendicular to the longitudinal axis 310, span a closed loop around the longitudinal axis. In the embodiment illustrated by FIG. 16, the closed loop is substantially closed. In other embodiments, the loop is completely closed. The substantially closed loop has one or more open portions. The aggregate open portion of the substantially closed loop is about 30 percent or less of the substantially closed loop. The energy source may supply energy to the independently controlled electrodes 306a, 306b, 308 of the transducer 300 simultaneously or sequentially or in an arbitrary order to produce the ablation zones 316a, 316b. In this way, tissue ablation or renal denervation or the like can be performed efficiently, effectively, and quickly, and in accordance with user selection.

In specific embodiments, the external electrodes span one or more open arc segments around the longitudinal axis, but all the external electrodes projected longitudinally onto any lateral plane which is perpendicular to the longitudinal axis span a substantially closed loop around the longitudinal axis.

Figure 17:
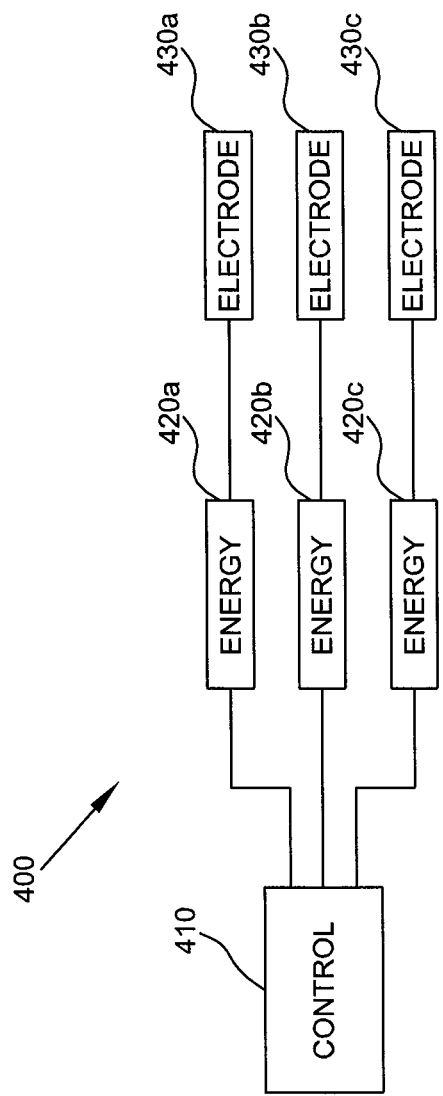
FIG. 17 is a block diagram of an ablation system according to one embodiment.

FIG. 17 is a block diagram of an ablation system 400 illustrating a control unit 410 which controls energy sources 420a, 420b, 420c to supply energy to the ultrasound transducer electrodes 430a, 430b, 430c to transmit ultrasonic energy for ablation. This embodiment shows a plurality of energy sources (420a, 420b, 420c) for supplying energy to independent electrodes (430a, 430b, 430c) for ablation simultaneously or independently. For example, the electrodes 430a, 430b are external, and the electrode 430c is internal. The energy sources 420a, 420b, 420c may come from a single energy generator.

Figure 18:
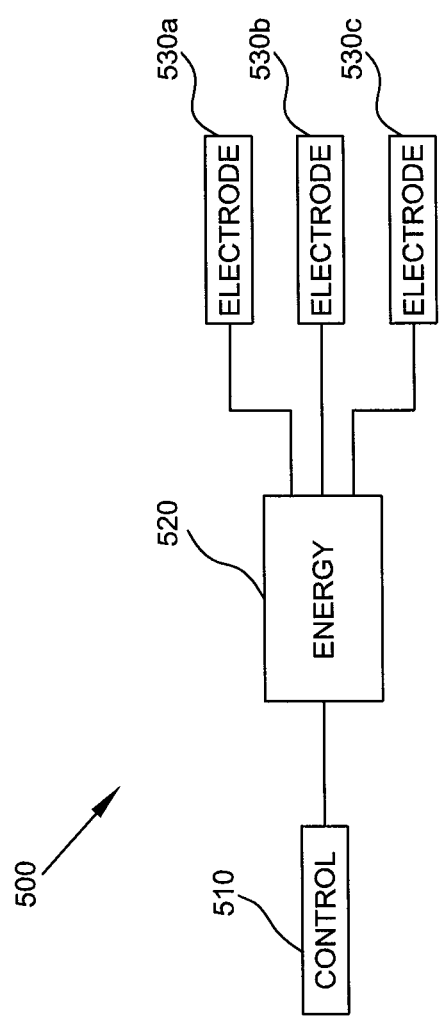
FIG. 18 is a block diagram of an ablation system according to another embodiment.

FIG. 18 is a block diagram of an ablation system 500 illustrating a control unit 510 which controls an energy source 520 to supply energy to the ultrasound transducer electrodes 530a, 530b, 530c to transmit ultrasonic energy for ablation. This embodiment shows a single energy source 520 for supplying energy to the electrodes (530a, 530b, 530c) for ablation simultaneously. For example, the electrodes 530a, 530b are external, and the electrode 530c is internal.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. An ablation apparatus comprising an ultrasonic transducer which includes:
   a piezoelectric element having a cylindrical shape with a longitudinal axis, an inner surface facing inwardly toward the longitudinal axis, and an outer surface facing outwardly away from the longitudinal axis, wherein the piezoelectric element is housed inside a bore formed within a tubular wall of a non-compliant and non-porous cap;
   a plurality of external electrodes disposed on the outer surface of the piezoelectric element; and
   at least one internal electrode disposed on the inner surface of the piezoelectric element;
   wherein the at least one internal electrode provides corresponding internal electrode portions that are disposed opposite the plurality of external electrodes with respect to the piezoelectric element, the external electrodes and the at least one internal electrode to be energized to apply an electric field across the piezoelectric element between the external electrodes and the corresponding internal electrode portions, so as to produce ultrasonic ablation zones extending from the energized external electrodes outwardly away from the longitudinal axis; and
   wherein the ultrasonic ablation zones of the external electrodes are distributed in a staggered configuration so as to span one or more open arc segments around the longitudinal axis, and the ultrasound ablation zones of all the external electrodes projected longitudinally onto any lateral plane which is perpendicular to the longitudinal axis span a substantially closed loop around the longitudinal axis.

2. The ablation apparatus of claim 1,
wherein the external electrodes are discretely spaced from each other at least one of longitudinally or laterally, and at least two of the external electrodes are spaced from one another longitudinally.

3. The ablation apparatus of claim 1,
wherein the external electrodes span one or more open arc segments around the longitudinal axis, and all the external electrodes projected longitudinally onto any lateral plane which is perpendicular to the longitudinal axis span a substantially closed loop around the longitudinal axis.

4. The ablation apparatus of claim 1,
wherein the external electrodes and the at least one internal electrode are independently controlled to be energized in one of simultaneous manner, sequential manner, and arbitrary manner to produce the ultrasonic ablation zones.

5. The ablation apparatus of claim 1,
wherein the external electrodes and the at least one internal electrode are energized by radiofrequency (RF) energy.

6. The ablation apparatus of claim 1,
wherein the cap contains a fluid therein for transmitting ultrasonic energy.

7. The ablation apparatus of claim 6,
wherein the cap has a fluid inlet for fluid flow into the cap and a fluid outlet for fluid flow out of the cap.

8. The ablation apparatus of claim 1, further comprising:
a handle assembly;
a shaft having a main lumen, a proximal end coupled to the handle assembly, and a distal end;
a distal tip section comprising the cap and coupled to the distal end of the shaft; and
an irrigation tube extending through the main lumen and having a distal end that terminates in the bore, the irrigation tube to supply irrigation fluid to the bore;
wherein the ultrasonic transducer is spaced apart from the wall of the cap.

9. The ablation apparatus of claim 8, further comprising:
a plurality of thermocouple wires that are connected to the cap.

10. The ablation apparatus of claim 8, further comprising:
a plurality of ring electrodes provided in a spaced-apart manner about the outer surface of the shaft adjacent the distal tip section.

11. The ablation apparatus of claim 8, further comprising:
an inner sleeve secured in the main lumen at the distal end of the shaft.

12. The ablation apparatus of claim 8, further comprising:
an inner supporting member that extends through the main lumen of the shaft and the bore of the cap.

13. The ablation apparatus of claim 1, further comprising:
a handle assembly;
a shaft having a main lumen, a proximal end coupled to the handle assembly, and a distal end;
an inner sleeve secured in the main lumen;

a distal tip section comprising the cap and coupled to the distal end of the shaft;

an inner supporting member that extends through the main lumen of the shaft and the bore of the cap; and an outer supporting member that extends through the inner sleeve and into the bore, with the inner supporting member housed in the outer supporting member;

wherein the ultrasonic transducer is spaced apart from the wall of the cap.

14. The ablation apparatus of claim 13, wherein the inner supporting member is selected from the group consisting of a coil, and a flat wire, and is made of a material selected from the group consisting of a metal, an alloy, and a polymer.

15. An ablation apparatus comprising a body having an axis and an ultrasonic transducer connected to the body, the ultrasonic transducer including:

a piezoelectric element coupled to the body, the piezoelectric element having a hollow interior, an inner surface facing the hollow interior, and an outer surface facing outwardly away from the hollow interior, wherein the piezoelectric element is housed inside a bore formed within a tubular wall of a non-compliant and non-porous cap;

a plurality of external electrodes disposed on the outer surface of the piezoelectric element; and at least one internal electrode disposed on the inner surface of the piezoelectric element;

wherein the at least one internal electrode provides corresponding internal electrode portions that correspond to the plurality of external electrodes, the external electrodes and the at least one internal electrode to be energized to apply an electric field across the piezoelectric element between the external electrodes and the corresponding internal electrode portions, so as to produce ultrasonic ablation zones extending from the energized external electrodes outwardly away from the hollow interior; and wherein the ultrasonic ablation zones of the external electrodes are distributed in a staggered configuration so as to span one or more open arc segments around the axis of the body, and the ultrasound ablation zones of all the external electrodes projected longitudinally onto any lateral plane which is perpendicular to the axis of the body span a substantially closed loop around the axis of the body.

16. The ablation apparatus of claim 15, wherein the external electrodes span one or more open arc segments around the axis of the body, and all the external electrodes projected longitudinally onto any lateral plane which is perpendicular to the axis of the body span a substantially closed loop around the axis of the body.

17. The ablation apparatus of claim 15, wherein the cap contains a fluid therein for transmitting ultrasonic energy.

18. An ablation apparatus comprising an ultrasonic transducer which includes:

a piezoelectric element having a cylindrical shape with a longitudinal axis, an inner surface facing inwardly toward the longitudinal axis, and an outer surface facing outwardly away from the longitudinal axis, wherein the piezoelectric element is housed inside an expandable element sized and configured with a predetermined fully expanded diameter that is less than a diameter of an area where ablation is to occur;

a plurality of external electrodes disposed on the outer surface of the piezoelectric element; and at least one internal electrode disposed on the inner surface of the piezoelectric element;

wherein the at least one internal electrode provides corresponding internal electrode portions that are disposed opposite the plurality of external electrodes with respect to the piezoelectric element, the external electrodes and the at least one internal electrode to be energized to apply an electric field across the piezoelectric element between the external electrodes and the corresponding internal electrode portions, so as to produce ultrasonic ablation zones extending from the energized external electrodes outwardly away from the longitudinal axis; and wherein the ultrasonic ablation zones of the external electrodes are distributed in a staggered configuration so as to span one or more open arc segments around the longitudinal axis, and the ultrasound ablation zones of all the external electrodes projected longitudinally onto any lateral plane which is perpendicular to the longitudinal axis span a substantially closed loop around the longitudinal axis.

19. The ablation apparatus of claim 18, further comprising:

a handle assembly;

a shaft having a proximal end coupled to the handle assembly, and a distal end, the shaft extending along an axis; and a distal ring provided at the distal end and oriented perpendicular to the axis of the shaft, the distal ring having a plurality of electrodes positioned in spaced-apart manner about the distal ring;

wherein the ultrasonic transducer is positioned spaced apart from the distal ring; and wherein the distal ring has a diameter that is greater than the fully expanded diameter of the expandable member.

20. The ablation apparatus of claim 19, further comprising:

an energy source coupled to the ultrasonic transducer; and means coupled to the plurality of electrodes for processing electrical signals received from the plurality of electrodes.

* * * * *